(12) United States Patent
Furumiya

(10) Patent No.: US 11,047,996 B2
(45) Date of Patent: Jun. 29, 2021

(54) PHOTODETECTOR

(71) Applicant: Shimadzu Corporation, Kyoto (JP)

(72) Inventor: Tetsuo Furumiya, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 16 days.

(21) Appl. No.: 16/474,206

(22) PCT Filed: Jun. 30, 2017

(86) PCT No.: PCT/JP2017/024202
§ 371 (c)(1),
(2) Date: Jun. 27, 2019

(87) PCT Pub. No.: WO2018/123112
PCT Pub. Date: Jul. 5, 2018

(65) Prior Publication Data
US 2020/0386901 A1    Dec. 10, 2020

(30) Foreign Application Priority Data

Dec. 27, 2016 (JP) .............................. JP2016-252571

(51) Int. Cl.
*G01T 1/29* (2006.01)
*A61B 6/03* (2006.01)
*A61B 6/00* (2006.01)

(52) U.S. Cl.
CPC ............ *G01T 1/2985* (2013.01); *A61B 6/037* (2013.01); *A61B 6/481* (2013.01)

(58) Field of Classification Search
CPC ........ G01T 1/2985; A61B 6/481; A61B 6/037
USPC .................................................. 250/363.04
See application file for complete search history.

(56) References Cited

U.S. PATENT DOCUMENTS

| | | | | |
|---|---|---|---|---|
| 4,335,374 A | * | 6/1982 | Nyuji | ..................... H03M 11/20 |
| | | | | 341/26 |
| 4,903,324 A | * | 2/1990 | Warnagiris | ............. H04B 7/005 |
| | | | | 379/24 |
| 7,045,789 B2 | * | 5/2006 | Ogawa | ................. A61B 6/4258 |
| | | | | 250/363.03 |

(Continued)

FOREIGN PATENT DOCUMENTS

| | | |
|---|---|---|
| JP | 2002-116256 A | 4/2002 |
| JP | 2006-179828 A | 7/2006 |

(Continued)

OTHER PUBLICATIONS

Written Opinion by the International Search Authority for PCT application PCT/JP2017/024202, dated Sep. 9, 2017.

(Continued)

*Primary Examiner* — David P Porta
*Assistant Examiner* — Gisselle M Gutierrez
(74) *Attorney, Agent, or Firm* — Muir Patent Law, PLLC

(57) ABSTRACT

This photodetector (100) includes a first discriminator (4) configured to discriminate a first signal output from a plurality of photoelectric conversion elements (1), a second discriminator (5) configured to discriminate a second signal based on signals output from the plurality of photoelectric conversion elements, and a trigger signal generator (7) configured to generate a trigger signal, the trigger signal indicating that light to be detected is incident based on discrimination results of the first discriminator and the second discriminator.

11 Claims, 12 Drawing Sheets

(56) References Cited

U.S. PATENT DOCUMENTS

| | | |
|---|---|---|
| 8,395,127 B1 | 3/2013 | Frach et al. |
| 9,040,898 B2 | 5/2015 | Henseler et al. |
| 9,568,360 B2 | 2/2017 | Furumiya |
| 10,175,369 B2* | 1/2019 | Fukuchi ............... G01T 1/2928 |
| 10,451,748 B1* | 10/2019 | Qiang ................... G01T 1/1644 |
| 2004/0139847 A1* | 7/2004 | Aiba ....................... G10K 15/12 84/722 |
| 2009/0121306 A1 | 5/2009 | Ishikawa |
| 2014/0048711 A1 | 2/2014 | Henseler et al. |
| 2015/0001399 A1 | 1/2015 | Fries et al. |
| 2015/0069250 A1 | 3/2015 | Schmand et al. |
| 2016/0299240 A1* | 10/2016 | Cho ........................ G01T 7/005 |
| 2018/0038966 A1* | 2/2018 | Fu ......................... G01T 1/2018 |
| 2018/0156926 A1* | 6/2018 | Frach .................... G01T 1/248 |

FOREIGN PATENT DOCUMENTS

| | | |
|---|---|---|
| JP | 2008-538606 A | 10/2008 |
| JP | 2012-060012 A | 3/2013 |
| WO | 2013/145011 A1 | 10/2013 |
| WO | 2014/173644 A1 | 10/2014 |

OTHER PUBLICATIONS

Buzhan et al., "Silicon photomultiplier and its possible applications", Nuclear Instruments and Methods in Physics Research A 504 (2003), pp. 48-52.

Extended European Search Report (EESR) dated Jun. 16, 2020 in the corresponding European patent application No. 17887587.8.

Notice of Reasons for Refusal dated Dec. 22, 2020 for corresponding Japanese Patent Application No. 2018-558653, submitted with a machine translation.

* cited by examiner

PHOTODETECTOR

TECHNICAL FIELD

The present invention relates to a photodetector, and more particularly, it relates to a photodetector including photoelectric conversion elements that operate in a Geiger mode.

BACKGROUND ART

Conventionally, a photodetector including photoelectric conversion elements that operate in a Geiger mode is known. Such a photodetector is disclosed in Japanese Patent Laid-Open No. 2012-60012, for example.

Japanese Patent Laid-Open No. 2012-60012 discloses a photodetector including an array (SiPM: Silicon Photomultipliers) of a plurality of avalanche photodiodes (photoelectric conversion elements) that operate in a Geiger mode in which a voltage equal to or higher than a breakdown voltage is applied, a plurality of discriminators that convert output signals from the avalanche photodiodes into rectangular pulses (binarized signals), respectively, and an adder that adds and outputs the rectangular pulses generated by the plurality of discriminators. This photodetector is configured to output a trigger signal indicating that light is incident when an addition signal (current) obtained by adding the rectangular pulses becomes three or more units (in a state in which three or more photons are incident on the avalanche photodiodes). On the other hand, when relatively small signals are output from the avalanche photodiodes due to noise such as dark current, the trigger signal is not output (falsely detected). Thus, it is possible to accurately detect that light is incident.

PRIOR ART

Patent Document

Patent Document 1: Japanese Patent Laid-Open No. 2012-60012

SUMMARY OF THE INVENTION

Problems to be Solved by the Invention

However, in the photodetector disclosed in Japanese Patent Laid-Open No. 2012-60012, the trigger signal indicating that light is incident when the addition signal (current) obtained by adding the rectangular pulses becomes 3 units or more is output, and thus the trigger signal is not output until three or more photons are incident. Thus, the trigger signal is output at the timing shifted from the timing at which the first photon is actually incident. Therefore, the photodetector disclosed in Japanese Patent Laid-Open No. 2012-60012 does not enable to accurately detect the precise time at which light, i.e. photon, is incident.

The present invention is intended to solve at least one of the above problems. The present invention aims to provide a photodetector capable of accurately detecting the precise time at which light is incident while significantly reducing or preventing false detection.

Means for Solving the Problems

In order to attain the aforementioned object, a photodetector according to an aspect of the present invention includes a plurality of photoelectric conversion elements configured to operate in a Geiger mode in which a voltage equal to or higher than a breakdown voltage is applied, and to output signals in response to light being incident thereon, a first discriminator configured to discriminate, using a first threshold, a first signal based on the signals output from the plurality of photoelectric conversion elements, a second discriminator configured to discriminate, using a second threshold larger than the first threshold, a second signal based on the signals output from the plurality of photoelectric conversion elements, and a trigger signal generator configured to generate a trigger signal, the trigger signal indicating that light to be detected is incident, the trigger signal being output when the first signal larger than the first threshold is input into the first discriminator and the second signal larger than the second threshold is input into the second discriminator.

In the photodetector according to this aspect of the present invention, as described above, the photodetector includes the trigger signal generator configured to generate the trigger signal indicating that the light to be detected is incident when the first discriminator discriminates that the first signal is larger than the first threshold and the second discriminator discriminates that the second signal is larger than the second threshold. Accordingly, the signal output from the photoelectric conversion elements based on the relatively large second threshold is discriminated such that false detection caused by noise (relatively small signal) can be significantly reduced or prevented. Furthermore, the timing at which it is discriminated that the first signal is larger than the first threshold substantially accurately reflects the time at which a photon is incident. Consequently, the trigger signal indicating that the light to be detected is incident is generated based on the signal from the first discriminator and the signal from the second discriminator such that the precise time at which the light is incident can be accurately detected while false detection is significantly reduced or prevented.

The aforementioned photodetector according to this aspect preferably further includes a delay unit provided between the first discriminator and the trigger signal generator, the delay unit being configured to delay a signal to be transmitted from the first discriminator to the trigger signal generator. The second threshold is larger than the first threshold, and thus the time taken for the second signal based on the signal output from the photoelectric conversion elements to reach the second threshold is longer than the time taken for the first signal output from the photoelectric conversion elements to reach the first threshold (the time for the second signal based on the signal output from the photoelectric conversion elements to reach the second threshold is later than the time for the first signal output from the photoelectric conversion elements to reach the first threshold). Therefore, the delay unit configured to delay the signal to be transmitted from the first discriminator to the trigger signal generator is provided between the first discriminator and the trigger signal generator such that the timing at which the first signal becomes High (H-level) can be later than the timing at which the second signal becomes High (H-level). Consequently, it is possible to more accurately achieve both detection of the precise time at which the light is incident and significant reduction in or prevention of false detection.

In the aforementioned photodetector according to this aspect, the second discriminator is preferably configured to discriminate whether or not a value of the second signal, which is a signal obtained by adding the first signal output from the plurality of photoelectric conversion elements, is larger than the second threshold. The first signal includes a signal corresponding to incidence of one photon or a weak signal due to noise. When photons are actually incident on the photodetector, a plurality of photons are incident around the same time. Accordingly, a plurality of first signals are (consecutively) generated around the same time, and thus the second signal is consecutively increased. On the other hand, noise occurs sporadically in the plurality of photoelectric conversion elements, and thus the second signal remains relatively small. Therefore, it is discriminated whether or not the value of the second signal, which is a signal obtained by adding the first signal output from the plurality of photoelectric conversion elements, is larger than the second threshold such that incidence of light can be accurately detected.

The aforementioned photodetector according to this aspect preferably further includes a binarization circuit provided in at least one of a region between each of the plurality of photoelectric conversion elements and the first discriminator and a region between each of the plurality of photoelectric conversion elements and the second discriminator, the binarization circuit being configured to binarize the signals output from the plurality of photoelectric conversion elements. The binarized signal (digital signal) has a relatively small processing load as compared with an unbinarized signal (analog signal). Therefore, the binarization circuit is provided in at least one of the region between each of the plurality of photoelectric conversion elements and the first discriminator and the region between each of the plurality of photoelectric conversion elements and the second discriminator such that the processing time taken to detect incidence of light can be reduced.

In this embodiment, the binarization circuit is preferably provided both between each of the plurality of photoelectric conversion elements and the first discriminator and between each of the plurality of photoelectric conversion elements and the second discriminator. According to this configuration, as compared with the case in which the binarization circuit is provided only between each of the plurality of photoelectric conversion elements and the first discriminator, the processing time taken to detect incidence of light can be further reduced.

In the aforementioned photodetector according to this aspect, the first discriminator and the second discriminator are preferably configured to discriminate the first signal and the second signal each including an analog signal. According to this configuration, it is not necessary to separately provide a circuit for digitizing (binarizing) the signals output from the photoelectric conversion elements, and thus the device configuration of the photodetector can be simplified.

In this embodiment, the photodetector preferably further includes a signal duplicator provided between the photoelectric conversion elements and each of the first discriminator and the second discriminator, the signal duplicator being configured to duplicate a signal same as the signals to be transmitted to the first discriminator and the second discriminator, and a signal indicting at least one of a position of each of the photoelectric conversion elements on which the light is incident and a total amount of the light incident on each of the photoelectric conversion elements (a value corresponding to the energy of incident gamma rays) is preferably sent with the signal duplicated by the signal duplicator. When at least one of the position of each of the photoelectric conversion elements on which the light is incident and the total amount of the light incident on each of the photoelectric conversion elements is acquired with a signal output to the outside of one of a plurality of photodetectors, the parasitic capacitance of each of the photoelectric conversion elements, the subsequent stage circuits, another photodetector, etc. constitute an unintended low-pass filter (LPF), and thus the signal output to the outside of one photodetector may be deteriorated. Therefore, at least one of the position of each of the photoelectric conversion elements on which the light is incident and the total amount of the light incident on each of the photoelectric conversion elements is insulated from another photodetector and acquired with the signal duplicated by the signal duplicator and insulated from the parasitic capacitance of each of the photoelectric conversion elements and the low-pass filter (LPF) formed by the subsequent stage circuits, another photodetector, etc. such that the position of each of the photoelectric conversion elements on which the light is incident and the total amount of the light incident on each of the photoelectric conversion elements can be acquired while the deterioration of the signal is significantly reduced or prevented. That is, at least one of the position of each of the photoelectric conversion elements on which the light is incident and the total amount of the light incident on each of the photoelectric conversion elements can be accurately acquired.

The aforementioned photodetector according to this aspect preferably further includes a plurality of channels each including a set of the photoelectric conversion elements, the first discriminator, the second discriminator, and the trigger signal generator, an OR gate configured to receive the trigger signal output from each of the channels, and a resistor matrix configured to receive a signal output from each of the channels and indicating at least one of a position of each of the photoelectric conversion elements on which the light is incident and a total amount of the light incident on each of the photoelectric conversion elements. According to this configuration, the trigger signal output from each of the channels and the signal indicating at least one of the position and the total amount of the light can be merged, and thus the processing load on the subsequent stage circuits (circuits that calculate the light incident timing, the total amount of the light, and the light incident position, for example) can be reduced.

The aforementioned photodetector according to this aspect is preferably used in a positron emission tomography apparatus. According to this configuration, the precise time at which the light based on gamma rays emitted due to electron-positron pair annihilation is incident can be more accurately detected.

Effect of the Invention

According to the present invention, as described above, it is possible to accurately detect the precise time at which the light is incident while significantly reducing or preventing false detection.

MODES FOR CARRYING OUT THE INVENTION

Embodiments embodying the present invention are hereinafter described on the basis of the drawings.

First Embodiment (Overall Configuration)

Figure 1:
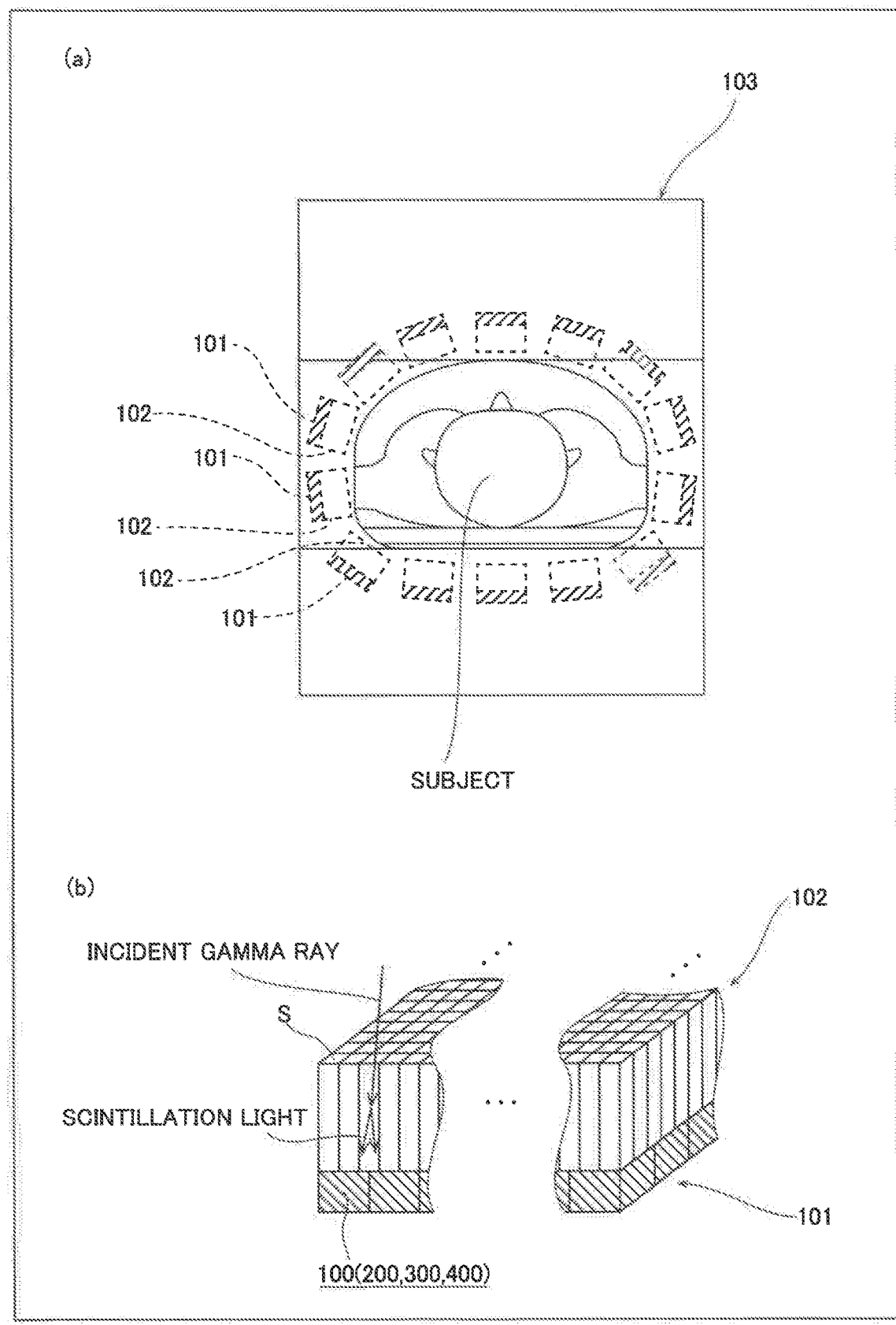
FIG. 1 is a diagram illustrating a positron emission tomography apparatus according to first and second embodiments of the present invention.

The configuration of a photodetector 100 according to a first embodiment of the present invention is now described with reference to FIG. 1. In the first embodiment, an example in which the photodetector 100 is used in a positron emission tomography apparatus (PET apparatus) 103 is described.

As shown in FIG. 1(a), the positron emission tomography apparatus 103 is an apparatus that images the inside of a subject (such as a human body) using a drug labeled with a positron-emitting radionuclide. Specifically, the positron emission tomography apparatus 103 is configured to acquire a position at which pair annihilation of the drug has occurred by detecting a pair of gamma rays (radiations) generated by the pair annihilation of electrons and positrons of the drug. Furthermore, the positron emission tomography apparatus 103 is configured to form (capture) an image of the inside of the subject by acquiring a plurality of positions at which the pair annihilation of the drug has occurred. The formed image is used for image diagnosis for determining the presence or absence of cancer cells, for example.

The photodetector 100 used in the positron emission tomography apparatus 103 is configured to image the subject in the supine position. Specifically, photodetectors 100 constitute a photodetector array 101 (see FIG. 1(b)) integrated in an array. A plurality of photodetectors 100 surround the periphery of the subject in a state in which the plurality of photodetectors 100 are directed to the body axis (an axis that extends from the head to the legs) of the subject. In addition, a plurality of photodetectors 100 are disposed with the same configuration also in a direction (the rearward direction of the plane of the figure) in which the body axis of the subject extends (not shown). The gamma rays generated by the pair annihilation of the drug are radiations of 511 keV, and cannot be directly detected by the photodetector 100. Therefore, a scintillator array 102 is provided between the subject and the photodetector 100 (photodetector array 101). Thus, as shown in FIG. 1(b), when a gamma ray is incident on a scintillator element S included in the scintillator array 102, a phosphor in the scintillator element S emits light by the gamma ray, and scintillation light is generated. The photodetector 100 is configured to detect the scintillation light emitted by the gamma ray. The photodetector array 101 and the scintillator array 102 are configured by integrating a plurality of minimum units in which scintillator elements S in five rows and five columns are provided for photodetectors 100 in two rows and two columns.

The configuration of the photodetector 100 according to the first embodiment of the present invention is now described with reference to FIGS. 2 to 8.

Figure 2:
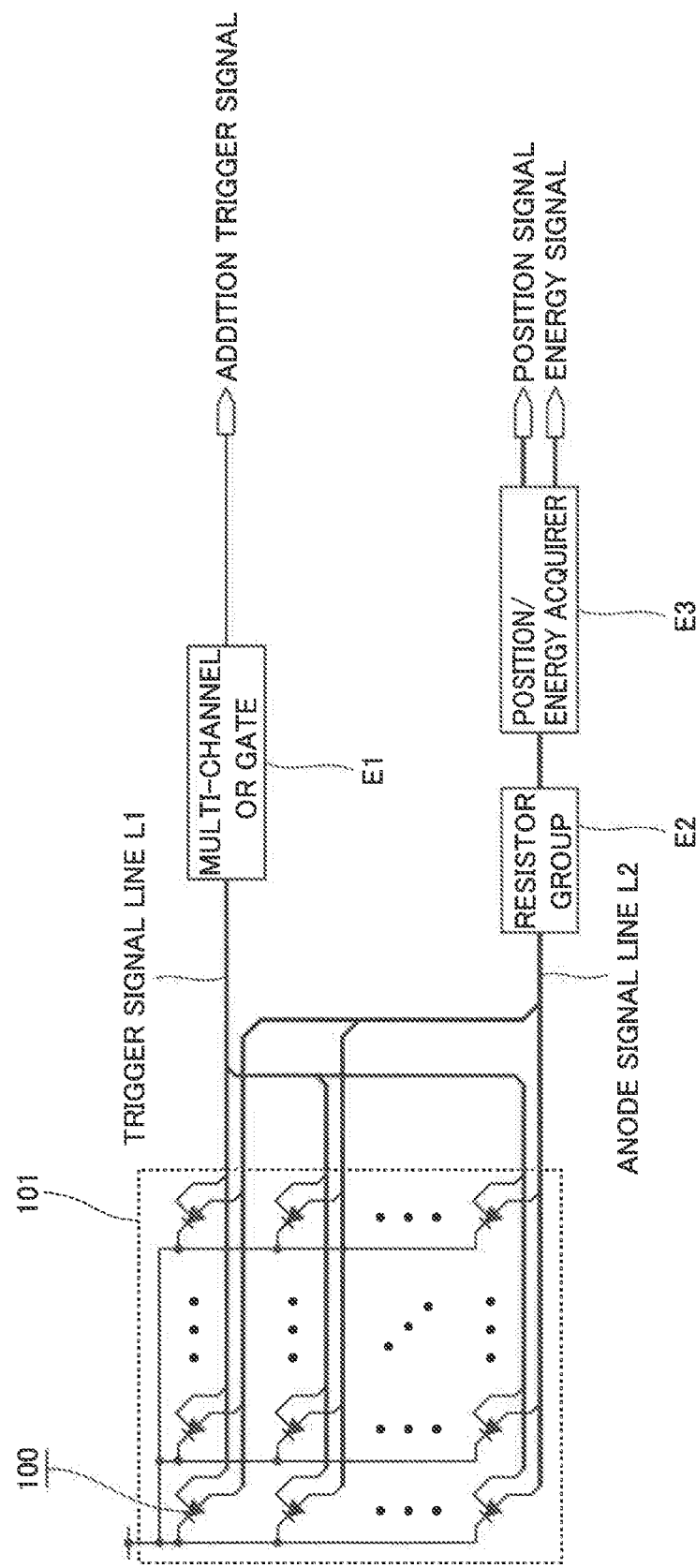
FIG. 2 is a block diagram showing the overall configuration of a photodetector in a multi-channel configuration according to the first embodiment of the present invention.

As shown in FIG. 2, the photodetectors 100 according to the first embodiment are included in the photodetector array 101 and are arranged in a matrix. The matrix (photodetector array 101) of the photodetectors 100 has eight rows and eight columns, the total number of which is sixty-four, for example. The photodetector array 101 includes a multi-channel OR gate E1, a resistor matrix E2, and a position/energy acquirer E3. One of a plurality of photodetectors 100 corresponds to one channel, and each channel includes a large number of photoelectric conversion elements 1 (described below; see FIG. 3). Furthermore, two signal lines (a trigger signal line L1 and an anode signal line L2) extend from each of the photodetectors 100. The trigger signal line L1, which is a first signal line, transmits a trigger signal SigTrig output from each of the photodetectors 100 to the multi-channel OR gate E1. The anode signal line L2, which is a second signal line, transmits an anode signal SigAn output from each of the photodetectors 100 to the resistor matrix E2. Each of the photodetectors 100 includes SiPMs (Silicon Photomultipliers), for example. Furthermore, in FIG. 2, portions of the signal lines indicated by thick lines are bus lines, and indicate that a plurality of signal lines extend independently of each other and along each other without being connected to each other.

The multi-channel OR gate E1 receives the trigger signal SigTrig, which is described below, output from each of the plurality of photodetectors 100. The trigger signal SigTrig output from each of the photodetectors 100 is output as a single addition trigger signal SigSumTrig from the multi-channel OR gate E1.

The resistor matrix E2 adjusts the current and/or voltage of the received anode signal SigAn output from each of the plurality of photodetectors 100, and outputs the adjusted signal to the position/energy acquirer E3.

The position/energy acquirer E3 calculates a position at which light is detected (a position corresponding to one photodetector 100) and the total amount of detected light based on the signal output from the resistor matrix E2 (the anode signal SigAn output from each of the photodetectors 100). The total amount of detected light corresponds to the energy of the gamma rays incident on the scintillator array 102. Therefore, the energy of the incident gamma rays can be calculated based on the calculated total amount of light. Then, a position signal SigPos related to the calculated position and an energy signal SigEn related to the total amount of light (the energy of the incident gamma rays) are output from the position/energy acquirer E3.

(Configuration of Photodetector)

The configuration of one photodetector 100 is now described with reference to FIG. 3. The configurations of the plurality of photodetectors 100 are the same as each other.

Figure 3:
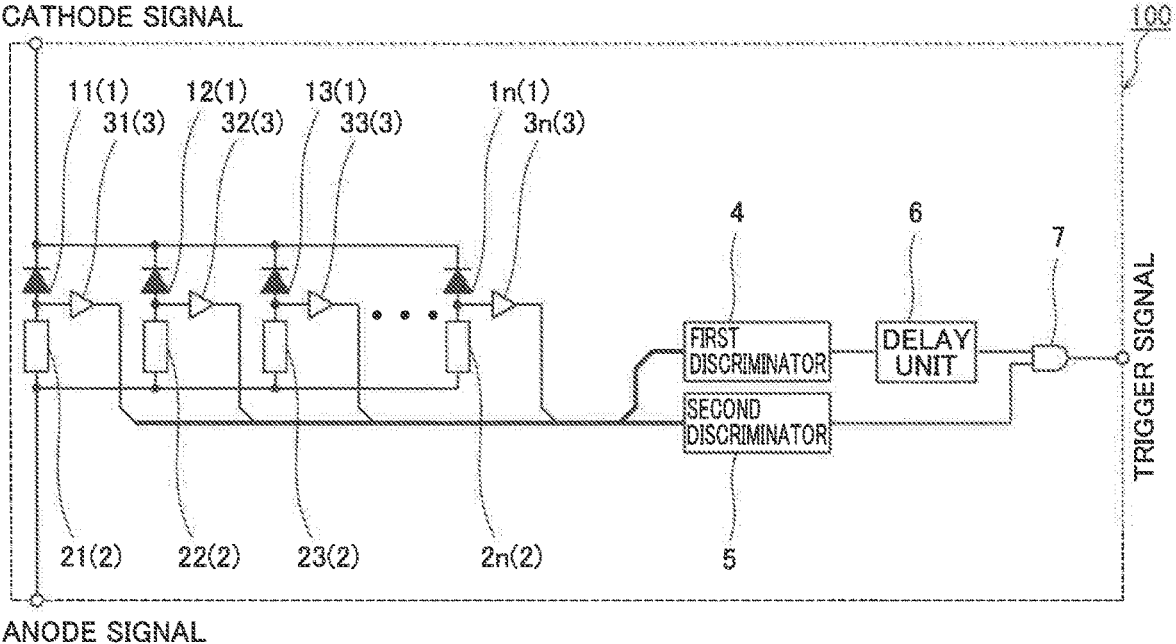
FIG. 3 is a diagram showing the configuration of the photodetector according to the first embodiment of the present invention.

As shown in FIG. 3, the photodetector 100 includes the photoelectric conversion elements 1 that operate in a Geiger mode in which a voltage equal to or higher than a breakdown voltage is applied, and that output signals in response to light being incident thereon. The photoelectric conversion elements 1 include avalanche photodiodes (APDs), for example. The photoelectric conversion elements 1 are semiconductors in which a reverse bias is applied to a p-n junction, and no current flows therethrough except for a dark current under normal conditions. When photons are incident on the photoelectric conversion elements 1, electron-hole pairs are generated by the photons, and a current flows therethrough. In the Geiger mode, the voltage that exceeds the breakdown voltage is applied such that chained generation of electron-hole pairs occurs, and thus the current increases rapidly and Geiger discharge occurs. Thus, the current having a good S/N ratio flows with respect to one incident photon (weak light), and thus photons can be detected with high accuracy.

The plurality of photoelectric conversion elements 1 (photoelectric conversion elements 11, 12, 13, . . . , and 1$n$: n represents the number of photoelectric conversion elements) are provided. The plurality of photoelectric conversion elements 1 are connected in parallel to each other.

The photodetector 100 also includes quenching elements 2 (21 to 2$n$). The quenching elements 2 are connected in series to the plurality of photoelectric conversion elements 1, respectively. When a current flows out of the photoelectric conversion element 1, a voltage is generated in the corresponding quenching element 2 (one of 21 to 2$n$) by the current. In this embodiment, the quenching element 2 reduces the voltage to be applied to the corresponding photoelectric conversion element 1 to less than the breakdown voltage. Thus, Geiger discharge in the photoelectric conversion element 1 is stopped. Consequently, a voltage equal to or higher than the breakdown voltage is again applied to the photoelectric conversion element 1. That is, the photoelectric conversion element 1 is returned to a state in which incidence of a photon can be detected. The quenching element 2 includes a resistor and/or a transistor, for example.

The photodetector 100 also includes binarization circuits 3. The binarization circuits 3 are connected between the anode sides of the plurality of photoelectric conversion elements 1 and the quenching elements 2. Furthermore, each of the binarization circuits 3 is provided between each of the photoelectric conversion elements 1 and a first discriminator 4 described below, and between each of the plurality of photoelectric conversion elements 1 and a second discriminator 5 described below. That is, each of the binarization circuits 3 is provided both between each of the plurality of photoelectric conversion elements 1 and the first discriminator and between each of the plurality of photoelectric conversion elements 1 and the second discriminator. Specifically, one common binarization circuit 3 is provided between one photoelectric conversion element 1 and the first discriminator and between one photoelectric conversion element 1 and the second discriminator.

When receiving voltage signals based on incidence of photons in the photoelectric conversion elements 1, the binarization circuits 3 output High (H-level, On) signal pulses. Specifically, the binarization circuits 3 are configured to output High (H-level, On) signals SigBin during a period in which the voltage signals received from the photoelectric conversion elements 1 exceed a binary threshold ThBin, and output Low (L-level, Off) signals SigBin during a period in which the voltage signals received from the photoelectric conversion elements 1 fall below the binary threshold ThBin. That is, the binarization circuits 3 output rectangular signals (pulses). Each of the binarization circuits 3 includes an inverter, for example.

Figure 4:
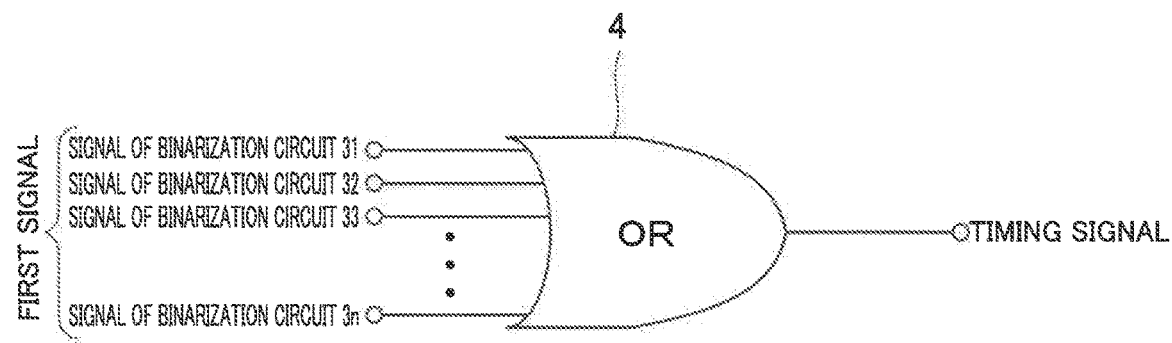
FIG. 4 is a diagram showing the configuration of a first discriminator according to the first embodiment of the present invention.

The photodetector 100 also includes the first discriminator 4 that discriminates a first signal Sig1 based on the signals output from the plurality of photoelectric conversion elements 1 using a first threshold Th1. Specifically, as shown in FIG. 4, the first discriminator 4 includes an OR gate that receives the first signal Sig1, which is an integration of the signals SigBin output from the plurality of binarization circuits 3 (31 to 3$n$). The first discriminator 4 outputs a High signal when the first signal Sig1 exceeds the first threshold Th1. The first threshold Th1 is set such that the first discriminator 4 outputs a High timing signal SigTim when any of the binarization circuits 3 outputs a High signal, and the first discriminator 4 outputs a Low timing signal SigTim when none of the binarization circuits 3 outputs a High signal. That is, the first discriminator 4 includes the OR gate, and thus the first discriminator 4 outputs the High timing signal SigTim during a period in which any of the signals output from the plurality of binarization circuits 3 is High, and outputs (discriminates) the Low timing signal SigTim during a period other than the above period. Therefore, the timing signal SigTim output from the first discriminator 4 is a rectangular signal (pulse).

The photodetector 100 also includes the second discriminator 5 that discriminates a second signal Sig2 based on the signals output from the photoelectric conversion elements 1 using a second threshold Th2, which is larger than the first threshold Th1. Specifically, the second discriminator 5 is configured to discriminate whether or not the value of the second signal Sig2, which is an integration of the signals SigBin output from the plurality of binarization circuits 3 (31 to 3$n$), is larger than the second threshold Th2. The signals SigBin output from a set of a plurality of common binarization circuits 3 (31 to 3$n$) are integrated and input into the first discriminator 4 and the second discriminator 5, and thus the first signal Sig1 and the second signal Sig2 are the same.

Figure 5:
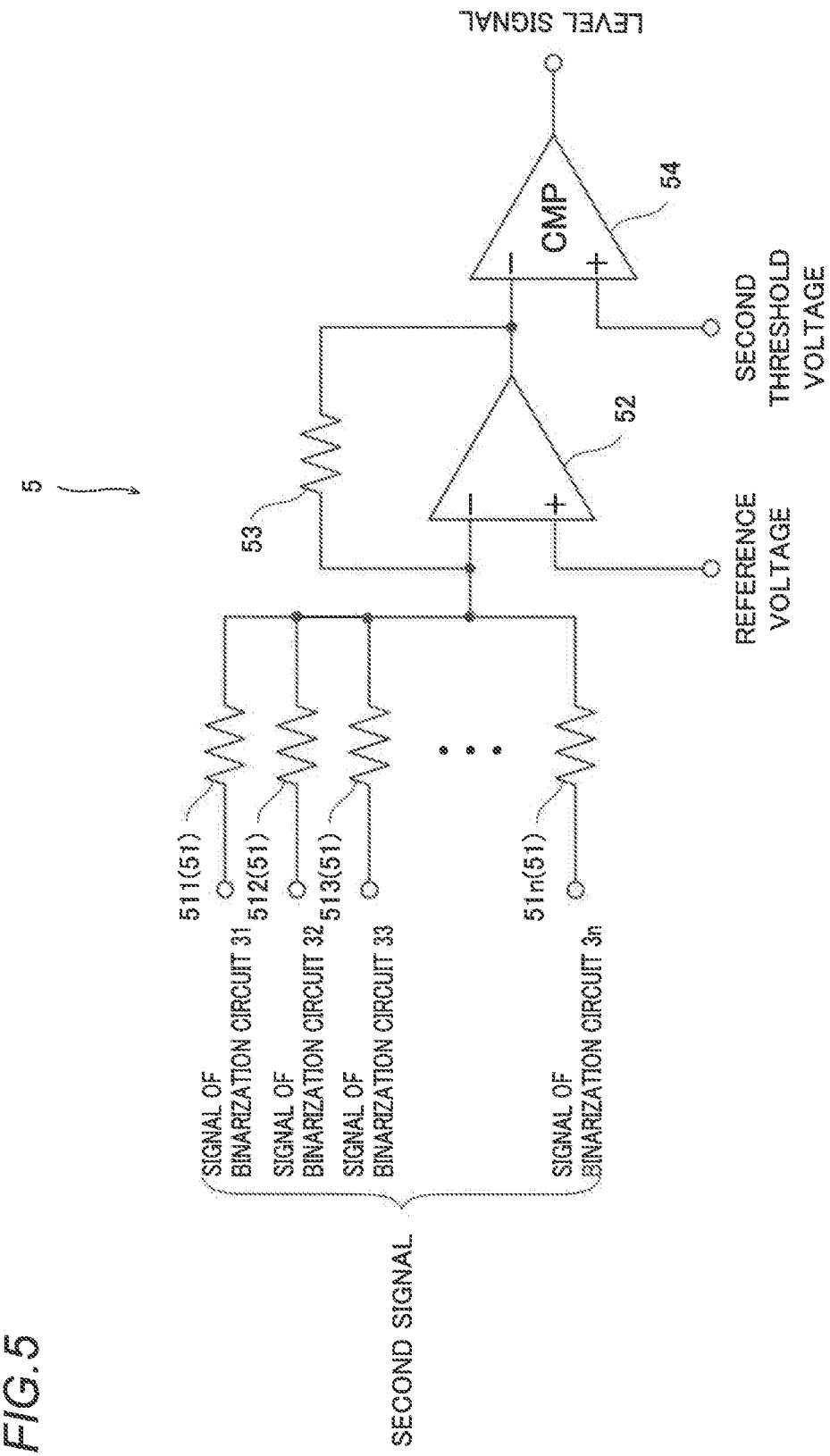
FIG. 5 is a diagram showing the configuration of a second discriminator according to the first embodiment of the present invention.

As shown in FIG. 5, the second discriminator 5 is configured to integrate the signals SigBin output from the plurality of binarization circuits 3 (31 to 3$n$), output a High level signal SigLev during a period in which the signal obtained by the integration exceeds the second threshold Th2, and output a Low level signal SigLev during a period in which the signal obtained by the integration falls below the second threshold Th2. The second threshold Th2 is set to a value corresponding to five High signals SigBin respectively output from the binarization circuits 3, for example. In this embodiment, the second signal Sig2 exceeds the second threshold during a period in which High signals are output from the five or more binarization circuits 3 (a period in which High periods of square waves of the five or more binarization circuits 3 overlap), and thus the second discriminator 5 outputs the High level signal SigLev. The second signal Sig2 does not reach the second threshold during a period other than the above period, and thus the second discriminator 5 outputs the Low level signal SigLev. The second discriminator 5 includes a plurality of resistors 51 (511, 512, 513, . . . , and 51n) so as to correspond to the plurality of binarization circuits 3 (31 to 3n). A voltage adder 52 adds, amplifies and outputs the binarized signals SigBin respectively input from the plurality of binarization circuits 3 (31 to 3n) via the resistors 51.

The second discriminator 5 includes a resistor 53. The resistor 53 is connected in parallel to the voltage adder 52, and adjusts the degree of amplification by the voltage adder 52.

The second discriminator 5 also includes a comparator (CMP) 54. The comparator 54 compares the voltage of the added signal output from the voltage adder 52 with the voltage of the second threshold Th2, outputs the High level signal SigLev when the voltage of the added signal exceeds the voltage of the second threshold Th2, and otherwise outputs the Low level signal SigLev.

As described above, an appropriate value (a value corresponding to five to ten incident photons, for example) is set as the second threshold Th2 to discriminate between noise and a signal such that it becomes possible to discriminate between a signal due to noise and a signal due to incidence of a photon and to perform signal processing appropriately. When the second threshold Th2 is set too large, a signal due to the scintillation light does not reach the second threshold Th2, and there is a possibility that detection of the scintillation light may be missed. When the second threshold Th2 is set too small, signals due to a plurality of noises generated at the same time exceed the second threshold Th2, and it becomes impossible to discriminate between scintillation light and noise. Therefore, the second threshold Th2 is set to a value corresponding to five to ten incident photons, for example. Thus, the second discriminator 5 does not react to the second signal Sig2 due to noise (does not output a High signal with respect to the second signal Sig2 due to noise). In addition, the second discriminator 5 outputs the High level signal SigLev during a period in which the second signal Sig2 exceeding the second threshold, which corresponds to incidence of a plurality of photons around the same time (consecutive incidence within a relatively short period of time), is received. The level signal SigLev output from the second discriminator 5 is a rectangular signal (pulse).

Note that the signal output from the voltage adder 52, which is an adder circuit, may have an upper limit value. The upper limit value needs to be larger than the second threshold Th2. Furthermore, the occurrence of noise is accidental, and thus the probability of noise occurring from the plurality of photoelectric conversion elements 1 around the same time becomes higher as the number of photoelectric conversion elements 1 included in the photodetector 100 increases. Therefore, the second threshold is set to an appropriate value in accordance with the size of the photodetector 100 (corresponding to the number of photoelectric conversion elements 1 included therein).

As shown in FIG. 3, the photodetector 100 is provided between the first discriminator 4 and a trigger signal generator 7 (described below), and includes a delay unit 6 configured to delay the timing signal SigTim to be transmitted from the first discriminator 4 to the trigger signal generator 7.

The delay unit 6 is configured to delay and output the timing signal SigTim input from the first discriminator 4. Consequently, the delay unit 6 outputs a delay timing signal SigDelTim obtained by delaying the timing at which the timing signal SigTim is switched between High and Low. At this time, the delay timing signal SigDelTim is output with a slight delay (several nanoseconds to several tens of nanoseconds, for example) from output of the level signal SigLev. The details are described below based on a timing chart in FIG. 7. The delay unit 6 includes a delay circuit, for example.

The photodetector 100 according to the first embodiment includes the trigger signal generator 7 that generates the trigger signal SigTrig indicating that light to be detected is incident when the first discriminator 4 discriminates that the first signal Sig1 is larger than the first threshold Th1 and the second discriminator 5 discriminates that the second signal Sig2 is larger than the second threshold Th2.

Figure 6:
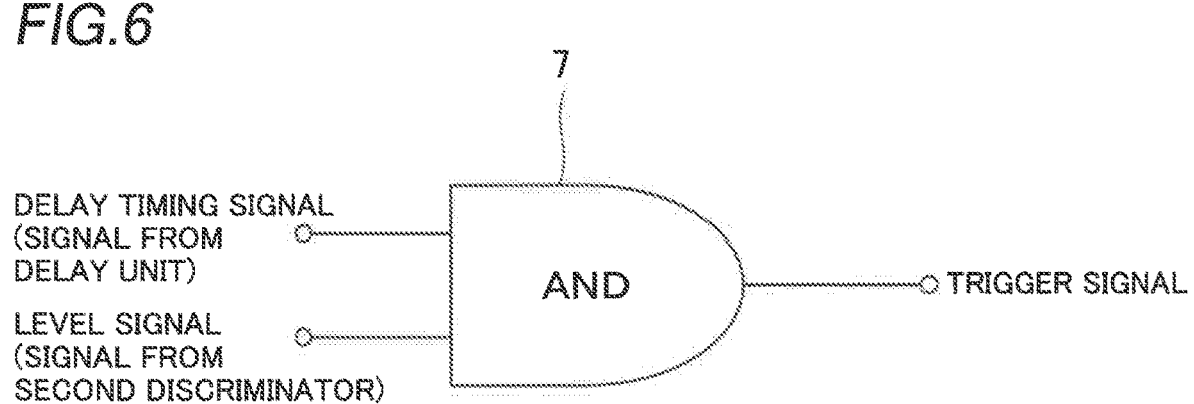
FIG. 6 is a diagram showing the configuration of a trigger signal generator according to the first embodiment of the present invention.

As shown in FIG. 6, the trigger signal generator 7 includes an AND gate. The trigger signal generator 7 receives the delay timing signal SigDelTim obtained by delaying the timing signal SigTim output from the first discriminator 4 by the delay unit 6 and the level signal SigLev output from the second discriminator 5. The trigger signal generator 7 is configured to generate a High trigger signal SigTrig during a period in which both the delay timing signal SigDelTim and the level signal SigLev are High, and to generate a Low trigger signal SigTrig during a period other than the above period. Then, the trigger signal SigTrig generated by the trigger signal generator is output to the multi-channel OR gate E1 (see FIG. 2).

(Timing Chart of Trigger Signal According to First Embodiment)

Figure 7:
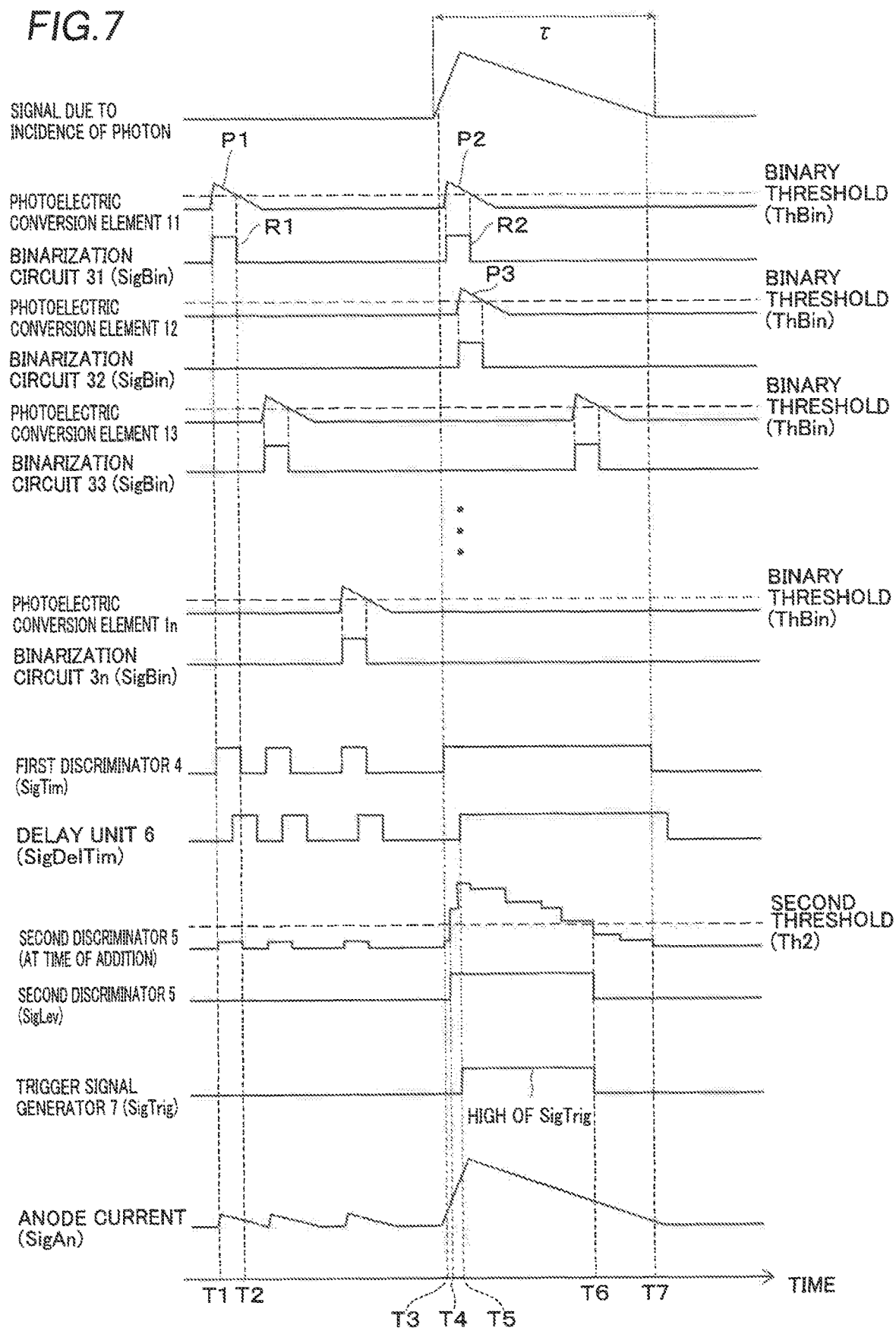
FIG. 7 is a time chart for illustrating generation of a trigger signal according to the first embodiment of the present invention.

Generation of the trigger signal SigTrig in the photodetector 100 (trigger signal generator 7) according to the first embodiment is now described with reference to FIG. 7. FIG. 7 shows the signals output from the respective locations in the photodetector 100 along a time axis. The left side of the chart shows the locations from which the signals are output. The top of the chart shows the light (signal) incident on the photodetector 100.

First, it is assumed that a pulse P1 (triangular pulse) is output from the photoelectric conversion element 11 due to noise such as dark current. Then, during a period from a time T1 to a time T2, the magnitude of the pulse P1 becomes larger than the binary threshold ThBin of the binarization circuit 3, and thus a High rectangular pulse R1 is output from the binarization circuit 3. Then, the High rectangular pulse R1 is input into the first discriminator 4. The first discriminator 4 includes the OR gate (that is, the first threshold Th1 of the first discriminator 4 has the same value as the binary threshold ThBin), and thus during the period from the time T1 to the time T2, the first discriminator 4 outputs the High rectangular pulse. On the other hand, the occurrence of noise such as dark current is sporadic, and thus the possibility of a plurality of (consecutive) occurrences around the same time is low. Therefore, the first signal Sig1 (second signal Sig2) input into the second discriminator 5 is not added (or is relatively small even if it is added), and thus the second signal Sig2 does not exceed the second threshold Th2. That is, the second discriminator 5 outputs a Low signal.

Next, it is assumed that light is incident on the photodetector 100 in a period τ. In this example, pulses P2, P3, . . . are respectively output from a plurality of photoelectric conversion elements 1 of the photoelectric conversion elements 11, 12, . . . , and 1n. The outputs of the plurality of pulses P2, P3, . . . occur consecutively. Specifically, first, at a time T3, the first signal Sig1 input into the first discriminator 4 exceeds the first threshold Th1, and thus the timing signal SigTim indicating the incident timing of a photon becomes High. At this point of time, the second signal Sig2 of the second discriminator 5 is smaller than the second threshold Th2, and thus the second discriminator 5 outputs a Low level signal SigLev.

Next, the pulses P3, . . . are consecutively output such that at a time T4, the second signal Sig2 of the second discriminator 5 exceeds the second threshold. Thus, the level signal SigLev output from the second discriminator 5 becomes High. Thereafter, after a time T5, the light incidence peaks, and then the light incidence gradually decreases. Then, at a time T6, the second signal Sig2 of the second discriminator 5 falls below the second threshold Th2, and thus the level signal SigLev output from the second discriminator 5 becomes Low. Then, at a time T7, the first signal Sig1 input into the first discriminator 4 disappears (falls below the first threshold Th1), and thus the timing signal SigTim output from the first discriminator 4 becomes Low.

The timing signal SigTim output from the first discriminator 4 is input into the delay unit 6. Thus, the delay unit 6 outputs the delay timing signal SigDelTim obtained by delaying the timing signal SigTim.

As to the timing signal SigTim, a High signal is output when one photon is incident. Therefore, the time taken for a signal to rise corresponds to the time from photon incidence to current generation, and is determined to be a substantially constant value. On the other hand, as to the level signal SigLev, a High signal is output when five photons are consecutively incident. However, the time from incidence of the first photon to incidence of the fifth photon through incidence of the second, third, and fourth photons varies, and thus the time taken for a signal to rise lengthens and becomes a relatively uncertain value. Therefore, the delay unit 6 delays the timing signal SigTim with respect to the level signal SigLev. Specifically, the rising timing (time T5) of the delay timing signal SigDelTim is later than the rising timing (time T4) of the level signal SigLev. It should be noted that when scintillation light (a bundle of photons) is actually incident due to incidence of gamma rays, signals are output from several hundreds to several tens of thousands of photoelectric conversion elements 1, for example.

Then, the trigger signal generator 7 generates the trigger signal SigTrig, which is the logical conjunction of the delay timing signal SigDelTim and the level signal SigLev. In FIG. 7, at the time T5 at which both the delay timing signal SigDelTim and the level signal SigLev are High, the trigger signal SigTrig becomes High. At the time T6 at which the level signal SigLev is Low, the trigger signal SigTrig becomes Low.

Thus, the trigger signal SigTrig becomes High (On) only when scintillation light is incident on the plurality of photoelectric conversion elements 1 (when the level signal SigLev is High). Thus, it is possible to distinguish between a signal due to noise and a signal due to incidence of light. Furthermore, the rising timing of the trigger signal SigTrig is aligned with the rising timing of the delay timing signal SigDelTim at the time T5. The delay time (delay circuit delay time), which is a substantially constant value, of the delay timing signal SigDelTim from the timing signal SigTim, and the delay time (propagation delay time), which is a substantially constant value, due to subsequent stage circuits are measured in advance. Thus, the known delay time is subtracted from the time at which the trigger signal SigTrig becomes High such that the rising (High) timing of the trigger signal SigTrig can be aligned with the rising timing of the timing signal SigTim. That is, the time at which a photon is first incident on the photodetector 100 can be acquired (calculated) substantially accurately. With the above configuration, the high accuracy of generation of the trigger signal SigTrig can be obtained from a simple readout circuit.

The photoelectric conversion element 1 constitutes an unintended pseudo capacitor (parasitic capacitance). Therefore, with respect to the anode signal SigAn of the photodetector 100, the parasitic capacitance and the subsequent stage circuits (the resistor matrix E2 and the position/energy acquirer E3) constitute an unintended low-pass filter (LPF). Furthermore, the parasitic capacitance of another photodetector 100 also affects the low-pass filter, and thus when the number of photodetectors 100 increases, the high-frequency component of a signal significantly disappears, and the signal is deteriorated. The trigger signal SigTrig is generated in the photodetector 100 (is isolated from another photodetector 100), and thus the influence of the parasitic capacitance of another photodetector 100 and the influence of noise generated from another photodetector 100 can be reduced. The signals of the photoelectric conversion elements 1 are input into the first discriminator 4 and the second discriminator 5 through the binarization circuits 3, and thus the trigger signal SigTrig can reduce the influence of the parasitic capacitance of each of the photoelectric conversion elements 1 also in the photodetector 100.

It is possible to accurately acquire information about the gamma rays due to the pair annihilation (electron-positron pair annihilation) of the drug from the precise time at which light is incident. Consequently, the positron emission tomography apparatus 103 can accurately acquire the position at which the pair annihilation of the drug has occurred.

(Accuracy of Trigger Signal)

Figure 8:
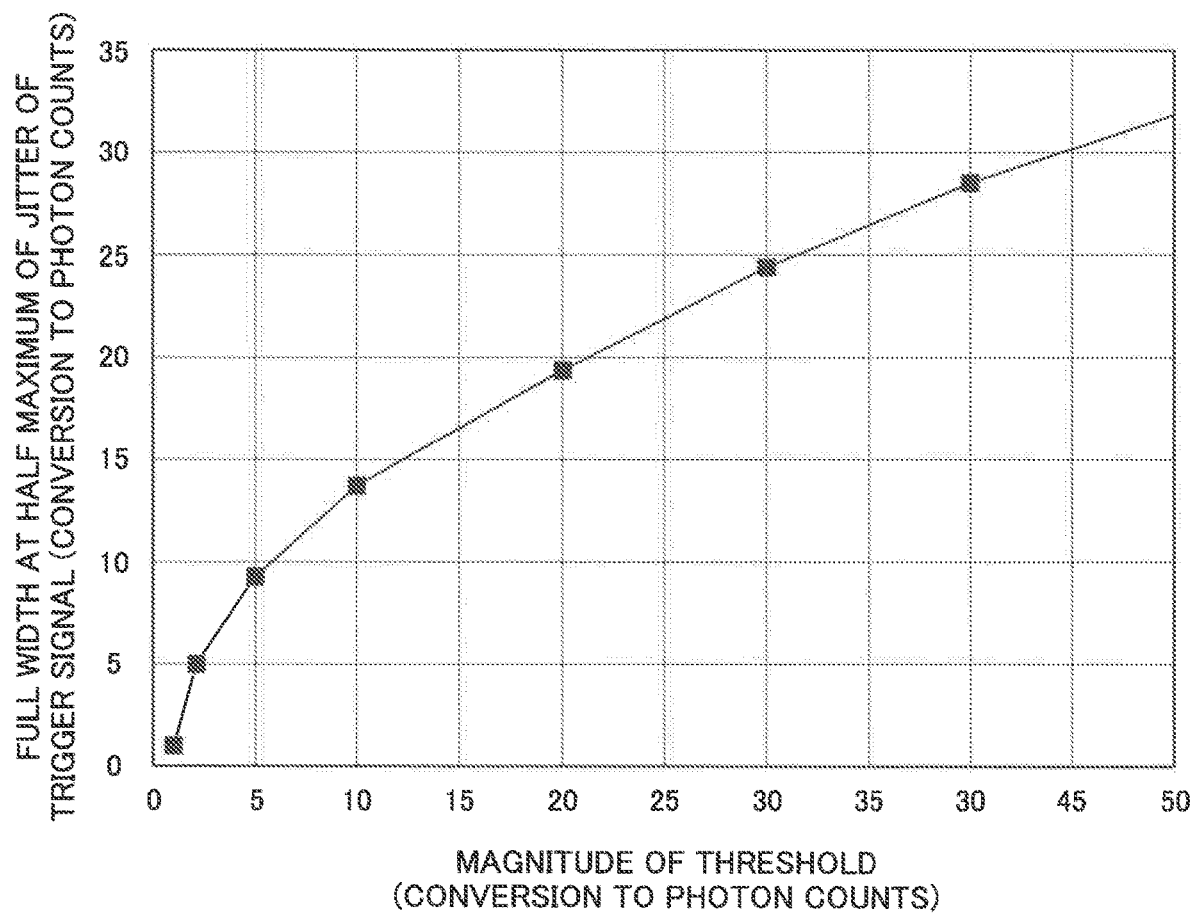
FIG. 8 is a graph showing the dependency of trigger accuracy on a first threshold when the photon detection probability of the photodetector according to the first embodiment of the present invention is 40%.

The dependency of the trigger accuracy on the threshold (in particular, the first threshold Th1 having a small value) is now described with reference to FIG. 8. A graph in FIG. 8 shows the results of a simulation in which the probability of detection when a plurality of photons are incident on the photodetector 100 is 40% per photon. For the sake of simplicity, the case in which a plurality of photons are incident simultaneously is considered. Furthermore, the horizontal axis of the graph represents values obtained by converting the magnitude of the threshold at which the trigger is High into the number of detected photons. The vertical axis of the graph represents values obtained by converting the full width at half maximum of the jitter of the trigger signal into the number of incident photons, and corresponds to the variation in the number of detected photons. As described above, as the number of photoelectric conversion elements 1 increases, the probability of noise occurring at the same time also increases. Therefore, as the threshold is increased, a fluctuation (error) is more likely to occur in the number of detected photons.

As described above, the detection timing of one photon is acquired using the first threshold Th1 corresponding to the detection of the photon with high trigger accuracy, and thus information about the timing at which the photon is incident can be accurately obtained. Thus, the time at which the gamma ray is incident can be accurately detected.

Advantages of First Embodiment

According to the first embodiment, the following advantages are obtained.

According to the first embodiment, as described above, the photodetector 100 includes the trigger signal generator 7 configured to generate the trigger signal SigTrig indicating that the light to be detected is incident when the first discriminator 4 discriminates that the first signal Sig1 is larger than the first threshold Th1 and the second discriminator 5 discriminates that the second signal Sig2 is larger than the second threshold Th2. Accordingly, the signal output from the photoelectric conversion elements 1 using the relatively large second threshold Th2 is discriminated such that false detection caused by noise (relatively small signal) can be significantly reduced or prevented. Furthermore, the timing at which it is discriminated that the first signal Sig1 is larger than the first threshold Th1 substantially accurately reflects the time at which the light is incident. Consequently, the trigger signal SigTrig indicating that the light to be detected is incident is generated based on the timing signal SigTrig from the first discriminator 4 and the level signal SigLev from the second discriminator 5 such that the precise time at which the light is incident can be accurately detected while false detection is significantly reduced or prevented.

According to the first embodiment, as described above, the photodetector 100 includes the delay unit 6 configured to delay the timing signal SigTrig to be transmitted from the first discriminator 4 to the trigger signal generator 7 between the first discriminator 4 and the trigger signal generator 7. The second threshold Th2 is larger than the first threshold Th1, and thus the time taken for the second signal Sig2 based on the signal output from the photoelectric conversion elements 1 to reach the second threshold Th2 is longer than the time taken for the first signal Sig1 output from the photoelectric conversion elements 1 to reach the first threshold Th1 (the time for the second signal Sig2 based on the signal output from the photoelectric conversion elements 1 to reach the second threshold Th2 is later than the time for the first signal Sig1 output from the photoelectric conversion elements 1 to reach the first threshold Th1). Therefore, the delay unit 6 configured to delay the timing signal SigTrig to be transmitted from the first discriminator 4 to the trigger signal generator 7 is provided between the first discriminator 4 and the trigger signal generator 7 such that the timing at which the first signal Sig1 becomes High can be later than the timing at which the second signal Sig2 becomes High. Consequently, it is possible to more accurately achieve both detection of the precise time at which the light is incident and significant reduction in or prevention of false detection.

According to the first embodiment, as described above, the second discriminator 5 is configured to discriminate whether or not the value of the second signal Sig2, which is a signal obtained by adding the first signal Sig1 output from the plurality of photoelectric conversion elements 1, is larger than the second threshold Th2. The first signal Sig1 includes a signal corresponding to incidence of one photon or a signal due to noise. When photons are actually incident on the photodetector 100, a plurality of photons are incident around the same time. Accordingly, a plurality of first signals Sig1 are (consecutively) generated around the same time, and thus the second signal Sig2 is consecutively increased. On the other hand, noise occurs sporadically in the plurality of photoelectric conversion elements 1, and thus the second signal Sig2 remains relatively small. Therefore, it is discriminated whether or not the value of the second signal Sig2, which is a signal obtained by adding the first signal Sig1 output from the plurality of photoelectric conversion elements 1, is larger than the second threshold Th2 such that incidence of light can be accurately detected.

According to the first embodiment, as described above, the photodetector 100 includes the binarization circuit 3 provided in at least a region between each of the plurality of photoelectric conversion elements 1 and the first discriminator 4 among the region between each of the plurality of photoelectric conversion elements 1 and the first discriminator 4 and a region between each of the plurality of photoelectric conversion elements 1 and the second discriminator 5 and configured to binarize the signal output from each of the plurality of photoelectric conversion elements 1. Accordingly, the binarized signal SigBin, which is a binarized signal (digital signal), has a relatively small processing load as compared with an unbinarized signal (analog signal). Therefore, the binarization circuit 3 is provided in at least the region between each of the plurality of photoelectric conversion elements 1 and the first discriminator 4 such that the processing time taken to detect incidence of light can be reduced.

According to the first embodiment, as described above, the common binarization circuit 3 is provided both between each of the plurality of photoelectric conversion elements 1 and the first discriminator 4 and between each of the plurality of photoelectric conversion elements 1 and the second discriminator. Accordingly, as compared with the case in which the binarization circuit 3 is provided only between each of the plurality of photoelectric conversion elements 1 and the first discriminator 4, the processing time taken to detect incidence of light can be further reduced.

According to the first embodiment, as described above, the photodetector 100 is used in the positron emission tomography apparatus (PET apparatus) 101. Accordingly, the precise time at which the light based on the gamma rays emitted due to the electron-positron pair annihilation is incident can be more accurately detected.

Second Embodiment

Figure 11:
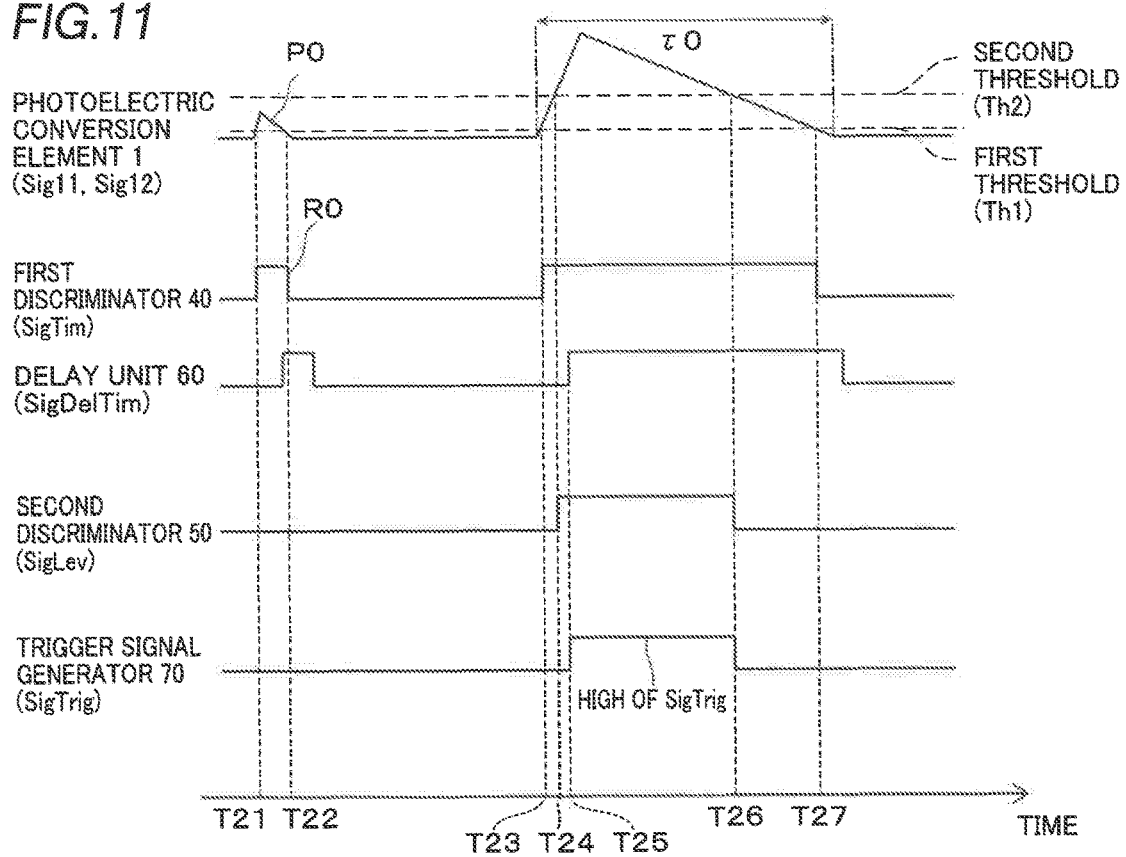
FIG. 11 is a time chart for illustrating generation of a trigger signal according to the second embodiment of the present invention.

The configuration of a photodetector 200 according to a second embodiment of the present invention is now described with reference to FIGS. 9 and 11. In the second embodiment, the photodetector 200 does not include binarization circuits 3 unlike the aforementioned first embodiment. Furthermore, in the second embodiment, the photodetector 200 includes a signal duplicator 8 unlike the aforementioned first embodiment. The same configurations as those of the first embodiment are denoted by the same reference numerals, and description thereof is omitted.

Figure 9:
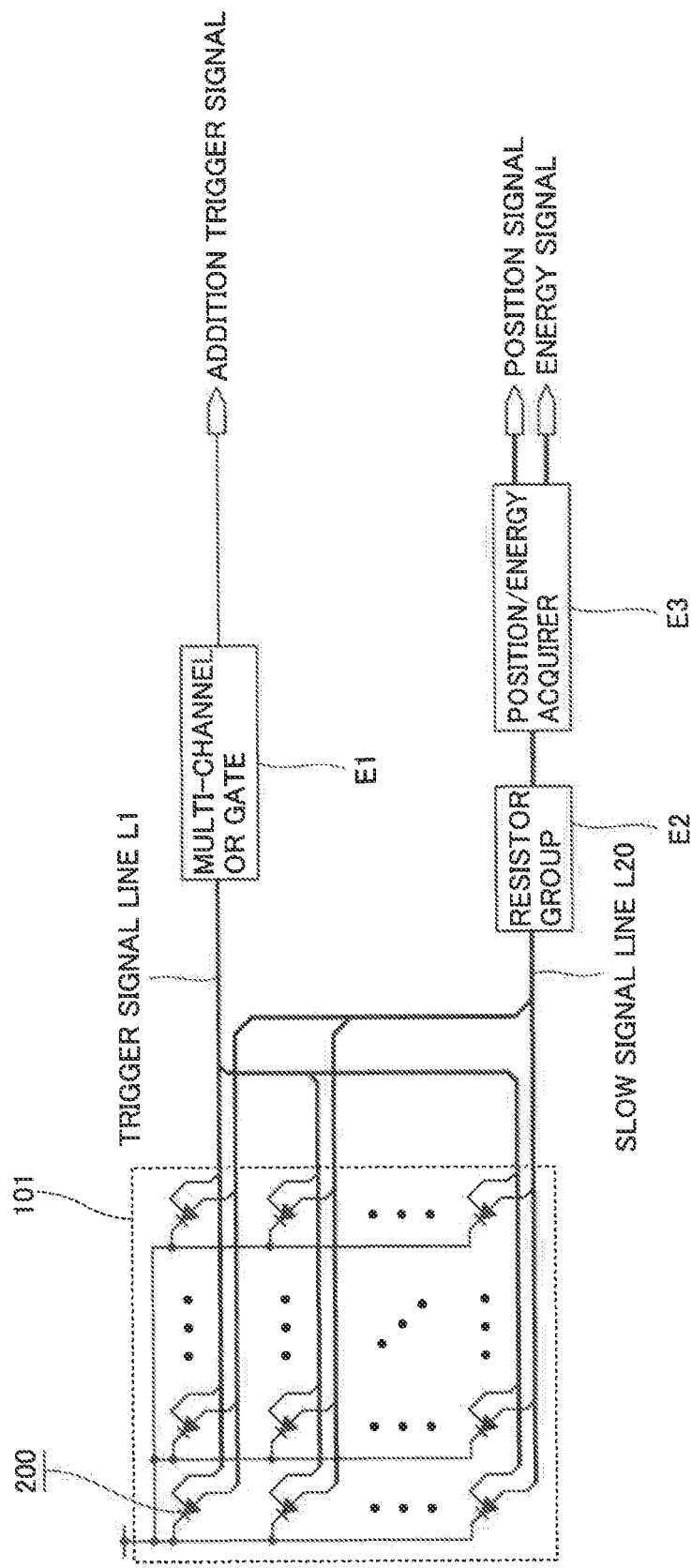
FIG. 9 is a block diagram showing the overall configuration of a photodetector in a multi-channel configuration according to the second embodiment of the present invention.

As shown in FIG. 9, photodetectors 200 according to the second embodiment are arranged in a matrix (eight rows and eight columns), and include a multi-channel OR gate E1, a resistor matrix E2, and a position/energy acquirer E3, as in the first embodiment. A detection signal (slow signal SigSlow) output from the photodetector 200 is input into the resistor matrix E2 via a slow signal line L20. The slow signal SigSlow is a signal obtained by duplicating an anode signal SigAn by the signal duplicator (described below; see FIG. 10).

Figure 10:
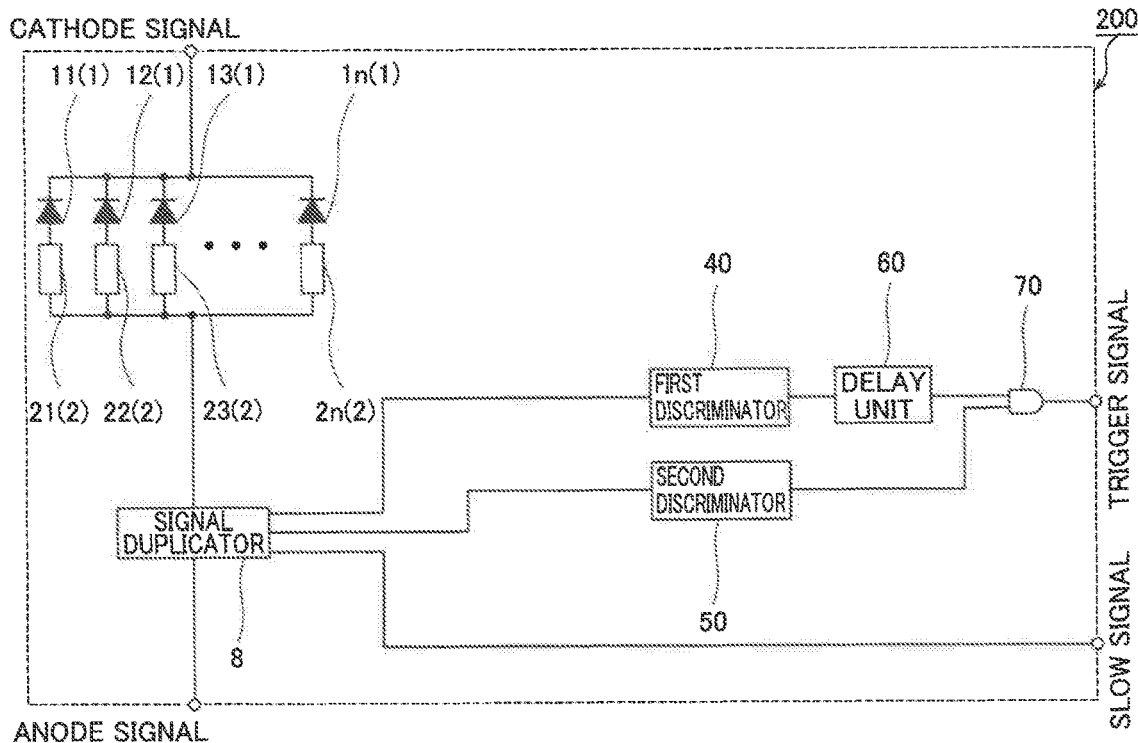
FIG. 10 is a diagram showing the configuration of the photodetector according to the second embodiment of the present invention.

As shown in FIG. 10, the photodetector 200 includes a plurality of photoelectric conversion elements 1, a plurality of quenching elements 2 (21 to 2n) respectively connected in series to the photoelectric conversion elements 1 (11 to 1n), the signal duplicator 8, a first discriminator 40, a second discriminator 50, and a trigger signal generator 70.

The first discriminator 40 and the second discriminator 50 are configured to discriminate a first signal Sig11 and a second signal Sig12 of analog signals output from the signal duplicator 8. The signal duplicator 8 is provided in common between the photoelectric conversion elements 1 and each of the first discriminator 40 and the second discriminator 50, and duplicates the same signal as the anode signal SigAn output from the photoelectric conversion elements 1. Furthermore, the photodetector 200 is configured to acquire the position of a photoelectric conversion element 1 on which light is incident and the total amount of light incident on the photoelectric conversion element 1 with the slow signal SigSlow duplicated by the signal duplicator 8. Specifically, the signal duplicator 8 outputs the first signal Sig11 to the first discriminator 40, outputs the second signal Sig12 to the second discriminator 50, and outputs the slow signal SigSlow to the resistor matrix E2. Note that the first signal Sign, the second signal Sig12, and the slow signal SigSlow are the same signals obtained by duplicating the anode signal SigAn, which is an integration of signals output from the photoelectric conversion elements 1.

The signal duplicator 8 duplicates and outputs the signals (anode signal SigAn) output from the photoelectric conversion elements such that the parasitic capacitance of the photoelectric conversion element $1n$ is insulated from the subsequent stage circuits (the resistor matrix E2 and the position/energy acquirer E3), and formation of a low-pass filter constituted by the parasitic capacitance of the photoelectric conversion element $1n$ and the subsequent stage circuits can be prevented. The duplicate signal is similarly insulated from the photoelectric conversion elements $1n$ of another photodetector 200, and thus it is not affected by the parasitic capacitance of the photoelectric conversion element $1n$ of another photodetector 200. Consequently, the interaction with another photodetector 200 can be reduced, and signal deterioration can be significantly reduced or prevented.

Specifically, when anode signals SigAn output from the (plurality of) photodetectors 200 are directly used to acquire the energy and position without providing the signal duplicator 8, the anode signals SigAn are affected by the parasitic capacitances (unintended formation of capacitors) of the photoelectric conversion elements 1 of the photodetectors 200 themselves, and the anode signals SigAn are deteriorated (the high frequency components are blurred). In this example, the signals output to generate a trigger signal SigTrig (the signals respectively output to the first discriminator 40 and the second discriminator 50) are also affected by the similar deterioration, and thus the trigger signal SigTrig finally output from the trigger signal generator 70 is also deteriorated. In addition, when the anode signal SigAn is directly used in the trigger signal generator 70 (because the input impedance of a circuit of the trigger signal generator 70 is not 0), the signal is similarly affected and deteriorated by the parasitic capacitance of the photoelectric conversion element $1n$.

Therefore, the signal duplicator 8 duplicates the anode signal SigAn output from the anode sides of the photoelectric conversion elements 1, and outputs signals equivalent to the anode signal SigAn to a signal line connected to the resistor matrix E2 (see FIG. 9), a signal line connected to the first discriminator 40, and a signal line connected to the second discriminator 50, respectively. The signal output to the resistor matrix E2 is the slow signal SigSlow. As in the first embodiment, the position/energy acquirer E3 calculates the position of the photodetector 200 that has detected the light and the total amount of the detected light (the energy of the incident gamma rays) based on the signal output from the resistor matrix E2 (the slow signal SigSlow output from each of the photodetectors 200). Then, a signal related to the calculated position and a signal related to the energy are output from the position/energy acquirer E3. The signals output to the first discriminator 40 and the second discriminator 50 are used to generate the trigger signal SigTrig.

Two duplicate signals respectively output from the signal duplicator 8 to the first discriminator 40 and the second discriminator 50 in order to generate the trigger signal SigTrig and duplicate signals output to the subsequent stage circuits in order to acquire the position and energy are insulated from the parasitic capacitance of the photoelectric conversion element $1n$ and an unintended low-pass filter (LPF) formed by the photoelectric conversion element $1n$, the subsequent stage circuits, and another photodetector 200. That is, the signals duplicated and insulated by the signal duplicator 8 are used to significantly reduce or prevent the influences of the parasitic capacitance and the low-pass filter on the trigger signal SigTrig and the slow signal SigSlow (deterioration of the trigger signal SigTrig and the slow signal SigSlow due to the parasitic capacitance and the low-pass filter). Furthermore, the trigger signal SigTrig and the slow signal SigSlow are insulated from each other, and thus interaction of the trigger signal SigTrig and the slow signal SigSlow with each other can be significantly reduced or prevented. When a plurality of photodetectors 200 are connected, even with the trigger signal generators 70 connected to each other (even with the merged trigger signals SifTrig), the influences that appear on the signals are minor due to the binarized trigger signals SigTrig (due to the trigger signals SigTrig multiple-insulated from the photoelectric conversion elements $1n$ of the photodetectors 200), and thus there is no problem. In addition, the signal duplicator 8 drives the subsequent stage circuits (the multi-channel OR gate E1, the resistor matrix E2, and the position/energy acquirer E3), and thus even with the slow signals SigSlow of the plurality of photodetectors 200 connected to each other (even with the merged slow signals SigSlow), the influences are minor such that there is no problem.

A terminal that outputs the anode signal SigAn not directly used for measurement is connected to a low impedance power supply or a ground potential (ground: GND) such that the terminal that outputs the anode signal SigAn does not form a low-pass filter due to the influence of the parasitic capacitance. When the anode signal SigAn is deteriorated, even the duplicated anode signal SigAn is in a deteriorated state, and thus it is necessary to duplicate the signal in a state in which the anode signal SigAn is not deteriorated.

The first discriminator 40 outputs a High timing signal SigTim during a period in which the input first signal Sig11 exceeds a first threshold Th1, and outputs a Low timing signal SigTim during a period in which the input first signal Sig11 falls below the first threshold Th1. The second discriminator 50 outputs a High level signal SigLev during a period in which the input second signal Sig12 exceeds a second threshold Th2, and outputs a Low level signal SigLev during a period in which the input second signal Sig12 falls below the second threshold Th2.

A delay unit 60 delays the timing signal SigTim output from the first discriminator 40, and outputs a delay timing signal SigDelTim. The rising timing (the timing at which the delay timing signal SigDelTim becomes High) of the delay timing signal SigDelTim is later than the rising timing of the level signal SigLev. The trigger signal generator 70 outputs a High trigger signal SigTrig when both the input delay timing signal SigDelTim and the input level signal SigLev become High, and otherwise outputs a Low trigger signal SigTrig. Thus, it is possible to distinguish between a signal due to noise and a signal due to incidence of light.

(Timing Chart of Trigger Signal According to Second Embodiment)

Generation of the trigger signal SigTrig of the photodetector 200 (trigger signal generator 70) according to the second embodiment is now described with reference to FIG. 11.

First, it is assumed that due to noise such as dark current, one pulse P0 corresponding to the signal of one photoelectric conversion element 1 is output from the photoelectric conversion element 1 to the signal duplicator 8, and the signal of the pulse P0 duplicated by the signal duplicator 8 is input into the first discriminator 40 and the second discriminator 50. That is, it is assumed that a signal corresponding to the signal of one photoelectric conversion element 1 (a duplicate signal of the pulse P0) is input as the first signal Sig11 into the first discriminator 40. In this example, the first signal Sig11 (the duplicate signal of the pulse P0) is larger than the first threshold Th1 of the first discriminator 40 during a period from a time T21 to a time T22, and thus the first discriminator 40 outputs a High timing signal SigTim, which is a rectangular pulse R0. On the other hand, a signal corresponding to the signal of one photoelectric conversion element 1 (a duplicate signal of the pulse P0) is similarly input as the second signal Sig12 into the second discriminator 50. In this example, the second signal Sig12 (the duplicate signal of the pulse P0) input into the second discriminator 50 does not exceed the second threshold Th2 corresponding to the case in which a plurality of pulses are added. That is, the second discriminator 50 does not output a High level signal SigLev, but outputs a Low level signal SigLev.

Next, it is assumed that light is incident on the photodetector 200 in a period τ0. In this example, pulses are consecutively output from a plurality of photoelectric conversion elements 1 of the photoelectric conversion elements 11, 12, . . . , 1n. Therefore, the second signal Sig12 (first signal Sign) becomes relatively large. Specifically, first, at a time T23, the first signal Sig11 input into the first discriminator 40 exceeds the first threshold Th1, and thus the timing signal SigTim indicating the incident timing of a photon becomes High. At this point of time, the second signal Sig12 of the second discriminator 50 is smaller than the second threshold Th2, and thus the second discriminator 5 outputs a Low level signal SigLev.

Next, at a time T24, the second signal Sig12 of the second discriminator 50 exceeds the second threshold Th2. Thus, the level signal SigLev output from the second discriminator 50 becomes High. Thereafter, after a time T25, the light incidence peaks, and then the light incidence gradually decreases. Then, at a time T26, the second signal Sig12 of the second discriminator 50 falls below the second threshold Th2, and thus the level signal SigLev output from the second discriminator 50 becomes Low. Then, at a time T27, the first signal Sig11 input into the first discriminator 40 disappears (falls below the first threshold Th1), and thus the timing signal SigTim output from the first discriminator 40 becomes Low.

The timing signal SigTim output from the first discriminator 40 is input into the delay unit 60. Thus, the delay unit 60 outputs the delay timing signal SigDelTim obtained by delaying the timing signal SigTim.

Then, the trigger signal generator 70 generates the trigger signal SigTrig, which is the logical conjunction of the delay timing signal SigDelTim and the level signal SigLev. In FIG. 11, at the time T25 at which both the delay timing signal SigDelTim and the level signal SigLev are High, the trigger signal SigTrig becomes High. At the time T26 at which the level signal SigLev is Low, the trigger signal SigTrig becomes Low. Thus, the trigger signal SigTrig is aligned with the delay timing signal SigDelTrig, the rising timing of which reflects the precise incidence time of the photon. Furthermore, the trigger signal SigTrig becomes High when the level signal SigLev not indicating noise but indicating incidence of the photon is High.

The remaining configurations of the second embodiment are similar to those of the first embodiment.

Advantages of Second Embodiment

According to the second embodiment, as described above, the first discriminator 40 and the second discriminator 50 are configured to discriminate the first signal Sig11 and the second signal Sig12 of analog signals. Accordingly, it is not necessary to separately provide a circuit for digitizing (binarizing) the signals output from the photoelectric conversion elements 1, and thus the device configuration of the photodetector 200 can be simplified.

According to the second embodiment, as described above, the photodetector 200 includes the signal duplicator 8 provided between the photoelectric conversion elements 1 and each of the first discriminator 40 and the second discriminator 50 and configured to duplicate the same signal as the anode signal SigAn output from the photoelectric conversion elements 1. Furthermore, the position of the photoelectric conversion element 1 on which light is incident and the total amount of light incident on the photoelectric conversion element 1 are acquired with the slow signal SigSlow duplicated by the signal duplicator 8. When at least one of the position of the photoelectric conversion element 1 on which light is incident and the total amount of light incident on the photoelectric conversion element 1 is acquired with a non-duplicated anode signal SigAn output to the outside of one of the plurality of photodetectors 200, the parasitic capacitance of the photoelectric conversion element 1, the subsequent stage circuits, another photodetector 200, etc. constitute an unintended low-pass filter (LPF), and thus the signal output to the outside of one photodetector 200 may be deteriorated. Therefore, at least one of the position of the photoelectric conversion element 1 on which light is incident and the total amount of light incident on the photoelectric conversion element 1 is acquired with the slow signal SigSlow duplicated by the signal duplicator 8 and insulated from the parasitic capacitance of the photoelectric conversion element 1 and the low-pass filter (LPF) formed by the subsequent stage circuits, another photodetector 200, etc. such that the position of the photoelectric conversion element 1 on which light is incident and the total amount of light incident on the photoelectric conversion element 1 can be acquired while the deterioration of the signal is significantly reduced or prevented. That is, the position of the photoelectric conversion element 1 on which light is incident and the total amount of light incident on the photoelectric conversion element 1 (the energy of the incident gamma rays) can be accurately acquired.

The remaining advantages of the second embodiment are similar to those of the first embodiment.

Third Embodiment

Figure 12:
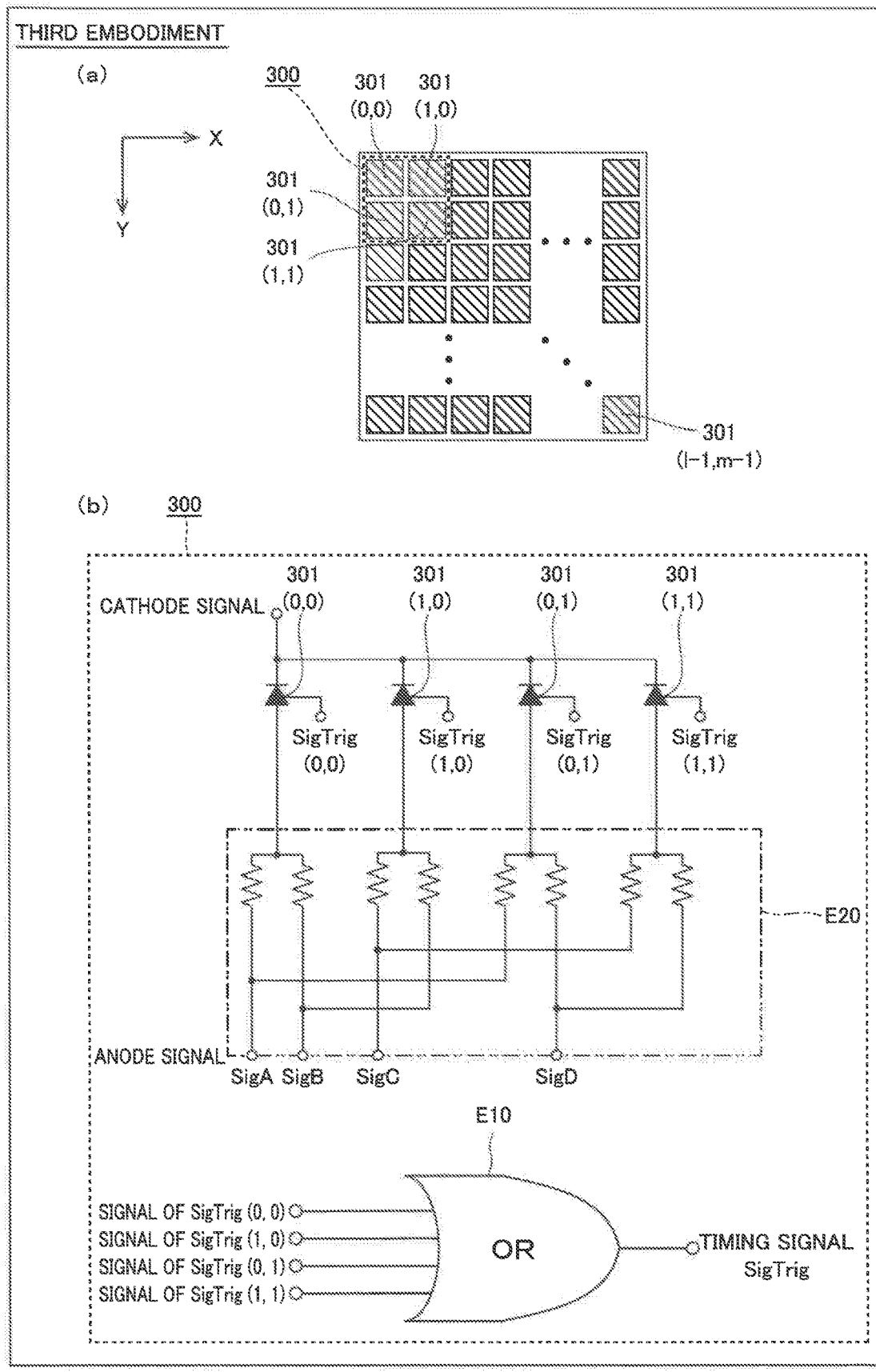
FIG. 12 is a diagram showing the configuration of a photodetector according to a third embodiment of the present invention.

The configuration of a photodetector 300 according to a third embodiment of the present invention is now described with reference to FIG. 12. The same configurations as those of the first embodiment are denoted by the same reference numerals, and description thereof is omitted.

As shown in FIG. 12(a), photodetector elements 301 are arranged in a matrix of 1 rows and m columns. Therefore, in order to indicate the position of each of the photodetector elements 301 in an X direction, any of numbers 0, 1, 2, ..., and 1-1 is given, and in order to indicate the position in a Y direction, any of numbers 0, 1, 2, ..., and m−1 is given. The photodetector 300 includes the photodetector elements 301 located at (0, 0), (0, 1), (1, 0), and (1, 1) ((X, Y)) corresponding to four (two rows and two columns) blocks. For example, when 1−1=7 and m−1=7, the photodetector elements 301 are arranged in a matrix of eight rows and eight columns.

The photodetector 300 includes four photodetector elements 301 each corresponding to one channel provided with a set of a plurality of photoelectric conversion elements 1, quenching elements 2 respectively connected in series to the plurality of photoelectric conversion elements 1, a first discriminator 4, a second discriminator 5, a delay unit 6, and a trigger signal generator 7. Specifically, one photodetector element 301 is configured to be equivalent to one photodetector 100 according to the first embodiment, for example. As shown in FIG. 12(b), the photodetector 300 further includes a resistor matrix E20 (not shown) that receives an anode signal SigAn output from each photodetector element 301 corresponding to the channel and indicating the position of the photoelectric conversion element 1 on which light is incident and the total amount of light incident on the photoelectric conversion element 1, and a multi-channel OR gate E10 (not shown) that receives a trigger signal SigTrig output from each photodetector element 301 corresponding to the channel. The multi-channel OR gate E10 is an example of an "OR gate" in the claims.

The multi-channel OR gate E10 integrates a plurality of trigger signals SigTrig (0, 0), (0, 1), (1, 0) and (1, 1) output from the connected photodetector elements 301, and outputs the same as a single trigger signal SigTrig. Furthermore, the resistor matrix E20 outputs the anode signals SigAn output from the connected photodetector elements 301 in accordance with the positions of the photodetector elements 301. Specifically, the signal of the photodetector element 301 located at (0, 0) is output as a signal SigA (corresponding to X=0) and a signal SigB (corresponding to Y=0), for example. The signal of the photodetector element 301 located at (0, 1) is output as a signal SigA (corresponding to X=0) and a signal SigD (corresponding to Y=1). That is, the resistor matrix E20 is configured to output a signal corresponding to information about the coordinates in the X direction and the Y direction. Thus, it is possible to acquire, in the subsequent stage circuits, which photodetector element 301 has output a signal.

The configuration of the photodetector 300 corresponding to a group of the above four (two rows and two columns) photodetector elements 301 is also applied to the other photodetector elements 301 individually (every four photodetector elements 301). With this configuration, as compared with the case in which trigger signals SigTrig and anode signals SigAn are merged into one and processed for all (sixty-four, for example) of photodetector elements 301 in 1 rows and m columns, the photodetector elements 301 are grouped in small units of four photodetector elements 301, and thus the processing load on the subsequent stage circuits (circuits that calculate the light incident timing, the total amount of light, and the light incident position, for example) is reduced. Note that the photodetector 300 may include a position/energy acquirer (not shown) that receives each of the above signals SigA to SigD output from the resistor matrix E20 of each of a plurality of photodetectors 300, and outputs a position signal indicating (specifying) the photodetector element 301 on which light is incident and an energy signal indicating the total amount of light incident on the photodetector element 301 (the energy of the incident gamma rays).

The remaining configurations of the third embodiment are similar to those of the first embodiment.

Advantages of Third Embodiment

According to the third embodiment, as described above, the photodetector 300 includes the plurality of photodetector elements 301 each corresponding to the channel including a set of the photoelectric conversion elements 1, the first discriminator 4, the second discriminator 5, and the trigger signal generator 7, and further includes the multi-channel OR gate E10 (OR gate) that receives the trigger signal SigTrig output from each photodetector element 301 corresponding to the channel and the resistor matrix E20 that receives the anode signal SigAn output from each photodetector element 301 corresponding to the channel and indicating the position of the photoelectric conversion element 1 on which light is incident and the total amount of light incident on the photoelectric conversion element 1 (the energy of the incident gamma rays). Accordingly, the trigger signal SigTrig output from each channel and the anode signal SigAn indicating at least one of the position and the energy can be merged, and thus the processing load on the subsequent stage circuits (circuits that calculate the light incident timing, the total amount of light, and the light incident position, for example) can be reduced.

The remaining advantages of the third embodiment are similar to those of the first embodiment.

MODIFIED EXAMPLES

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the example in which the delay unit 6 is provided between the first discriminator 4 and the trigger signal generator 7 has been shown in each of the aforementioned first and second embodiments, the present invention is not limited to this. For example, the delay unit 6 may be provided inside the first discriminator 4.

While the example in which the photodetectors 100 (200) are arranged in a matrix of eight rows and eight columns (sixty-four in total) has been shown in each of the aforementioned first and second embodiments, the present invention is not limited to this. According to the present invention, for example, the number of photodetectors 100 (200, 300) may be other than sixty-four, or the photodetectors 100 (200) may be arranged in a state (such as one row) other than a matrix.

While the example in which the photodetector array 101 and the scintillator array 102 are configured by integrating a plurality of minimum units in which the scintillator elements S in five rows and five columns are provided for the photodetectors 100 in two rows and two columns has been shown in each of the aforementioned first and second embodiments, the present invention is not limited to this. According to the present invention, for example, the number of photodetectors 100 (200) and the number of scintillator elements S, which are relative to each other, may be any numbers (the scintillator elements S in four rows and four columns are provided for the photodetectors 100 (200) in three rows and three columns, for example). Alternatively, one scintillator element S may be provided for one photodetector 100. Furthermore, one scintillator element S may be provided for the entire photodetector array 101 including the photodetectors 100 (200). In addition, there may not be a fixed correspondence in number between the photodetectors 100 (200) and the scintillator elements S.

While the delay time for the timing signal SigTim by the delay unit 6 (60) is set to a constant value in each of the aforementioned first and second embodiments, the present invention is not limited to this. For example, the delay time may be adjusted for each photodetector 100 (200).

While the example in which the first threshold Th1 is adjusted to a value corresponding to a signal indicating incidence of one photon has been shown in each of the aforementioned first and second embodiments, the present invention is not limited to this. For example, the first threshold Th1 may be adjusted to a value corresponding to signals indicating incidence of any number of photons other than one photon.

While the example in which the second threshold Th2 is adjusted to a value corresponding to signals indicating incidence of five to ten photons has been shown in each of the aforementioned first and second embodiments, the present invention is not limited to this. For example, the first threshold Th1 may be adjusted to a value corresponding to signals indicating incidence of any number of photons other than five to ten photons.

While the example in which the first threshold Th1 and the second threshold Th2 are set to the same values across all the photodetectors 100 (200) has been shown in each of the aforementioned first and second embodiments, the present invention is not limited to this. For example, the first threshold Th1 and the second threshold Th2 may be adjusted for each photodetector 100 (200).

While the example in which the first discriminator 4 (40) includes an OR gate has been shown in each of the aforementioned first and second embodiments, the present invention is not limited to this. For example, the first discriminator 4 (40) may include a voltage adder 52 or the like, similarly to the second discriminator 5 (50). Note that the OR gate is more advantageous in terms of circuit response speed and circuit miniaturization.

While the example in which the position and the energy are acquired based on the anode signal SigAn output from the anode sides of the photoelectric conversion elements 1 has been shown in each of the aforementioned first and second embodiments, the present invention is not limited to this. For example, the position and the energy may be acquired from the length of the time during which the signal exceeds the corresponding threshold and a time difference based on the signal output from the first discriminator 4 (40) or the second discriminator 5 (50). Alternatively, the position and the energy may be acquired based on a cathode signal output from the cathode sides of the photoelectric conversion elements 1. Specifically, the multi-channel OR gate E1, the resistor matrix E2, and the position/energy acquirer E3 may be connected to the cathode signal side. In this example, the quenching elements 2 connected to the photoelectric conversion elements, the binarization circuits 3, the first discriminator 4 (40), the second discriminator 5 (50), the delay unit 6 (60), the trigger signal generator 7 (70), and the circuit contributing to generation of the trigger signal SigTrig, such as the signal duplicator 8, are similarly connected to the cathode sides of the photoelectric conversion elements 1.

Figure 13:
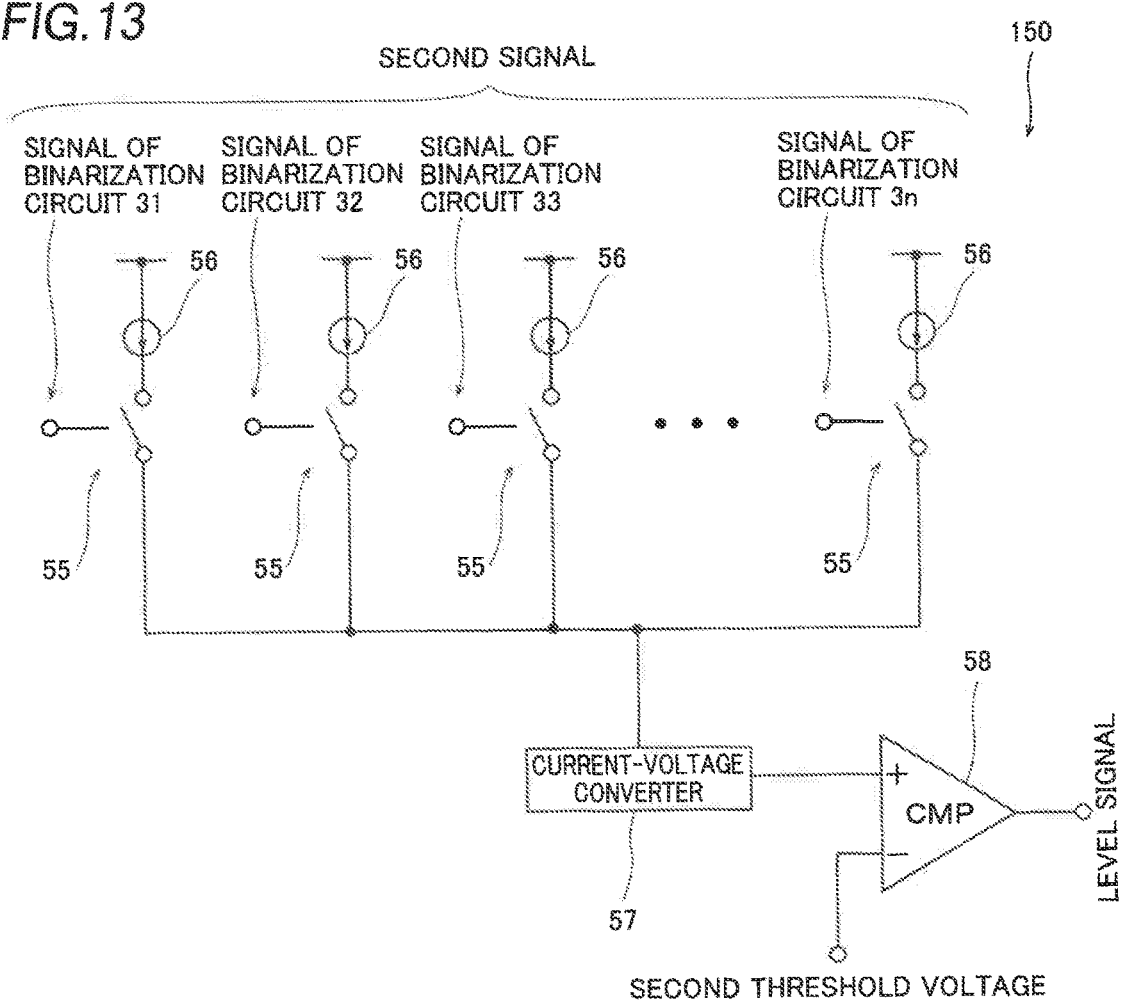
FIG. 13 is a diagram showing a second discriminator according to a modified example of the first embodiment of the present invention.

While the example in which the second discriminator 5 is configured to add the voltage signals output from the binarization circuits 3 or the photoelectric conversion elements 1 with the voltage adder 52 and discriminate the same, as shown in FIG. 5, has been shown in the aforementioned first embodiment, the present invention is not limited to this. According to the present invention, a second discriminator 150 may include switches 55, current sources 56, a current-voltage converter 57, and a comparator 58 as shown in FIG. 13. The switches 55 are a group of switches respectively connected to binarization circuits 3 or photoelectric conversion elements 1, and turn on when light is detected in the corresponding photoelectric conversion elements 1, and send current signals. The current-voltage converter 57 converts the current signals output from the photoelectric conversion elements 1 into voltage signals. The comparator 58 outputs a High level signal SigLev only when a voltage exceeding a second threshold Th2 is input.

While the example in which the photodetector 100 (200) is used in a positron emission tomography apparatus has been shown in each of the aforementioned first and second embodiments, the present invention is not limited to this. According to the present invention, for example, the photodetector 100 (200) may be used to detect light in a gamma camera, spectroscopic analysis, inspection of manufactured components, a distance measuring device, and another measurement/exploration.

Figure 14:
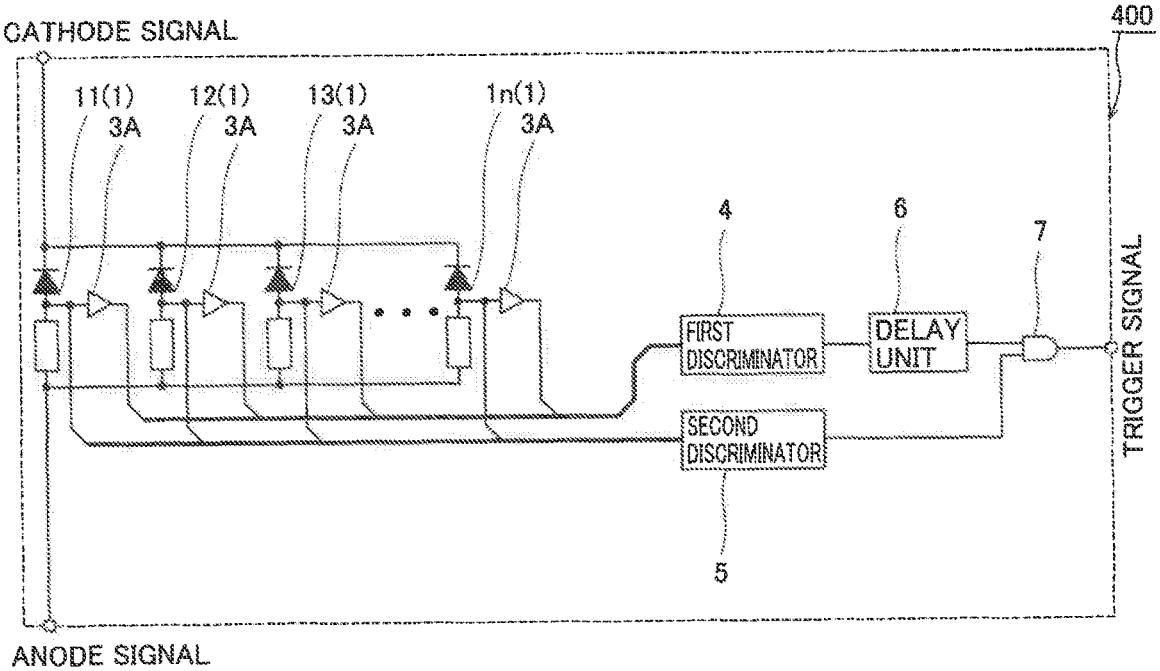
FIG. 14 is a diagram showing a photodetector according to another modified example of the first embodiment of the present invention.
Figure 15:
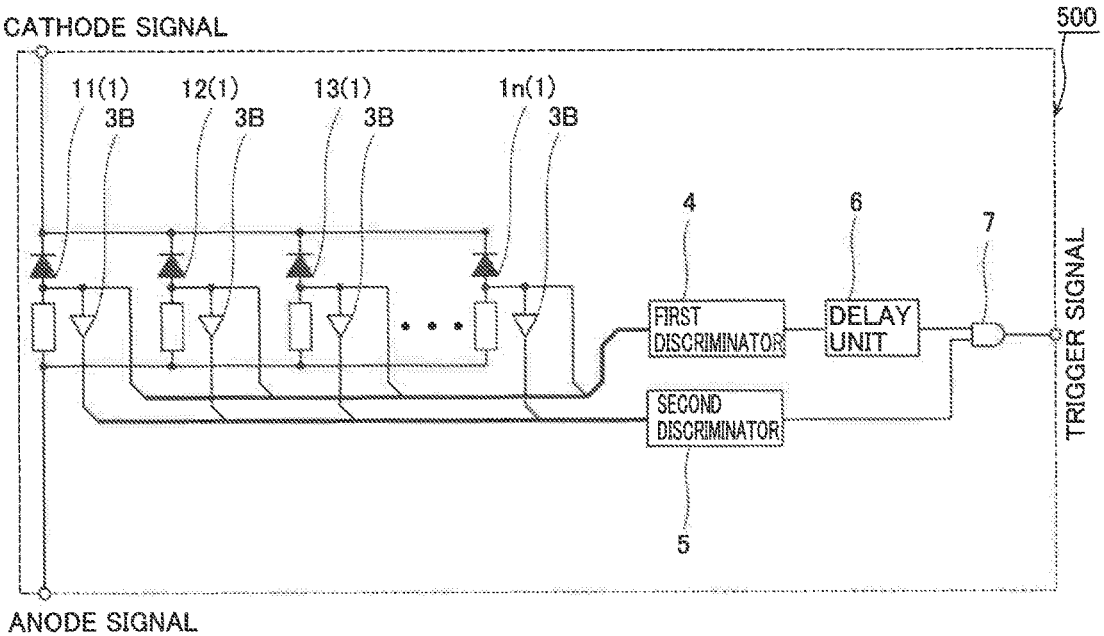
FIG. 15 is a diagram showing a photodetector according to yet another modified example of the first embodiment of the present invention.
Figure 16:
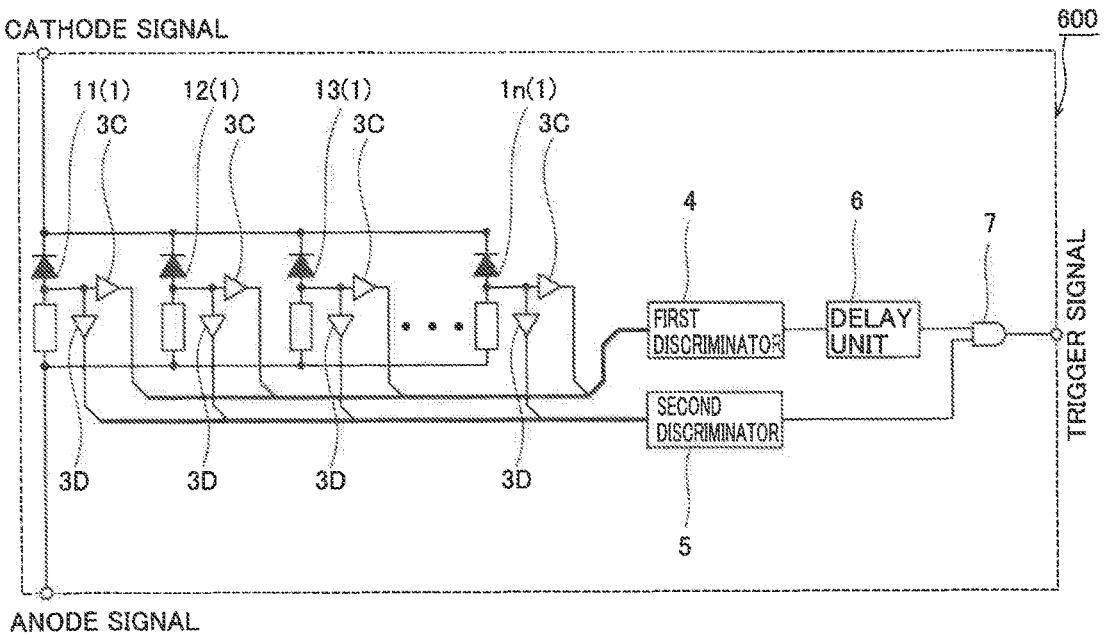
FIG. 16 is a diagram showing a photodetector according to still another modified example of the first embodiment of the present invention.

While the example in which the common binarization circuit 3 is provided between each of the plurality of photoelectric conversion elements 1 and the first discriminator 4 and between each of the plurality of photoelectric conversion elements 1 and the second discriminator 5 has been shown in the aforementioned first embodiment, the present invention is not limited to this. According to the present invention, as in a photodetector 400 shown in FIG. 14, a binarization circuit 3A may be provided only between each of photoelectric conversion elements 1 and a first discriminator 4. In this example, a signal is slightly delayed in the process of binarizing the signal by the binarization circuit 3A. Therefore, when the binarization circuit 3A is provided only for the first discriminator, only the timing signal SigTim output from the first discriminator, the rising of which is faster than that of the level signal SigLev by the second discriminator, is slightly delayed in the process of binarization. Thus, a time difference between the rising of the level signal SigLev and the rising of the timing signal SigTim can be reduced. Alternatively, as in a photodetector 500 shown in FIG. 15, a binarization circuit 3B may be provided only between each of photoelectric conversion elements 1 and a second discriminator 5. In addition, as in a photodetector 600 shown in FIG. 16, separate binarization circuits 3C and 3D may be respectively provided between each of photoelectric conversion elements 1 and a second discriminator 5 and between each of the photoelectric conversion elements 1 and a second discriminator 5. In the photodetectors 400, 500, and 600 shown in FIGS. 14 to 16, a first signal and a second signal are different from each other unlike the case in which the common binarization circuit 3 is provided between each of the photoelectric conversion elements 1 and the second discriminator 5 and between each of the photoelectric conversion elements 1 and the second discriminator 5, to which a signal SigBin output from the same binarization circuit 3 is input.

While the example in which the trigger signals SigTrig and the anode signal SigAn, which is a signal indicating the position and the total amount of incident light (the energy of the incident gamma rays), are merged for every four photodetector elements 301 in two rows and two columns has been shown in the aforementioned third embodiment, the present invention is not limited to this. According to the present invention, a unit by which the trigger signals SigTrig and the anode signal SigAn are merged may not be four. Furthermore, grouping of the photodetector elements 301 is not limited to grouping in a matrix, but the photodetector elements 301 may be grouped one-dimensionally in each column or row.

While the example in which one photodetector element 301 is configured to be equivalent to one photodetector 100 according to the first embodiment has been shown in the aforementioned third embodiment, the present invention is not limited to this. According to the present invention, one photodetector element 301 may be configured to be equivalent to one photodetector 200 according to the second embodiment.

DESCRIPTION OF REFERENCE NUMERALS

1: photoelectric conversion element
3, 3A, 3B, 3C: binarization circuit
4, 40: first discriminator
5, 50: second discriminator
6, 60: delay unit
7, 70: trigger signal generator
8: signal duplicator
100, 200, 300, 400, 500, 600: photodetector
103: positron emission tomography apparatus (PET apparatus)
301: photodetector element (channel)
E1, E10: multi-channel OR gate (OR gate)
E2, E20: resistor matrix

The invention claimed is:

1. A photodetector comprising:
a plurality of photoelectric conversion elements configured to operate in a Geiger mode in which a voltage equal to or higher than a breakdown voltage is applied, and to output signals in response to light being incident thereon;
a first discriminator configured to discriminate, using a first threshold, a first signal based on the signals output from the plurality of photoelectric conversion elements;
a second discriminator configured to discriminate, using a second threshold larger than the first threshold, a second signal obtained by adding signals based on the signals output from the same plurality of photoelectric conversion elements as the plurality of photoelectric conversion elements; and
a trigger signal generator configured to generate a trigger signal, the trigger signal indicating that light to be detected is incident, the trigger signal being output when the first signal larger than the first threshold is input into the first discriminator and the second signal larger than the second threshold is input into the second discriminator.

2. The photodetector according to claim 1, further comprising a delay unit provided between the first discriminator and the trigger signal generator, the delay unit being configured to delay a signal to be transmitted from the first discriminator to the trigger signal generator.

3. The photodetector according to claim 1, wherein the second discriminator is configured to discriminate whether or not a value of the second signal, which is a signal obtained by adding the first signals output from the plurality of photoelectric conversion elements, is larger than the second threshold.

4. The photodetector according to claim 1, further comprising a binarization circuit provided in at least one of a region between each of the plurality of photoelectric conversion elements and the first discriminator and a region between each of the plurality of photoelectric conversion elements and the second discriminator, the binarization circuit being configured to binarize the signals output from the plurality of photoelectric conversion elements.

5. The photodetector according to claim 4, wherein the binarization circuit is provided both between each of the plurality of photoelectric conversion elements and the first discriminator and between each of the plurality of photoelectric conversion elements and the second discriminator.

6. The photodetector according to claim 1, wherein the first discriminator and the second discriminator are configured to discriminate the first signal and the second signal each including an analog signal.

7. The photodetector according to claim 6, further comprising a signal duplicator provided between the photoelectric conversion elements and each of the first discriminator and the second discriminator, the signal duplicator being configured to duplicate a signal same as the signals output from the photoelectric conversion elements; wherein
a signal indicting at least one of a position of each of the photoelectric conversion elements on which the light is incident and a total amount of the light incident on each of the photoelectric conversion elements is output with the signal duplicated by the signal duplicator.

8. The photodetector according to claim 1, further comprising:
a plurality of channels each including a set of the photoelectric conversion elements, the first discriminator, the second discriminator, and the trigger signal generator;
an OR gate configured to receive the trigger signal output from each of the channels; and
a resistor matrix configured to receive a signal output from each of the channels and indicating at least one of a position of each of the photoelectric conversion elements on which the light is incident and a total amount of the light incident on each of the photoelectric conversion elements.

9. A positron emission tomography apparatus comprising the photodetector according to claim 1.

10. The photodetector according to claim 4, wherein the first discriminator includes an OR gate that receives signals output from a plurality of binarization circuits, each binarization circuit being identical to the binarization circuit.

11. A photodetector comprising:
a plurality of photoelectric conversion elements configured to operate in a Geiger mode in which a voltage equal to or higher than a breakdown voltage is applied, and to output signals in response to light being incident thereon;
a first discriminator configured to discriminate, using a first threshold, a first signal based on the signals output from the plurality of photoelectric conversion elements;
a second discriminator configured to discriminate, using a second threshold larger than the first threshold, a second signal based on the signals output from the plurality of photoelectric conversion elements;

a trigger signal generator configured to generate a trigger signal, the trigger signal indicating that light to be detected is incident, the trigger signal being output when the first signal larger than the first threshold is input into the first discriminator and the second signal larger than the second threshold is input into the second discriminator; and a delay unit provided between the first discriminator and the trigger signal generator, the delay unit being configured to delay a signal to be transmitted from the first discriminator to the trigger signal generator.

* * * * *